US009389320B2

(12) United States Patent
Ogawa et al.

(10) Patent No.: US 9,389,320 B2
(45) Date of Patent: Jul. 12, 2016

(54) RADIATION DETECTOR, AND RADIATION IMAGING APPARATUS PROVIDED WITH DETECTOR

(75) Inventors: Koichi Ogawa, Tokyo (JP); Tsutomu Yamakawa, Osaka (JP); Daisuke Hashimoto, Osaka (JP); Tatsuya Nagano, Osaka (JP); Hideyuki Nagaoka, Osaka (JP); Masahiro Tsujita, Osaka (JP)

(73) Assignee: TAKARA TELESYSTEMS CORP., Osaka-Shi, Osaka (JP)

( * ) Notice: Subject to any disclaimer, the term of this patent is extended or adjusted under 35 U.S.C. 154(b) by 83 days.

(21) Appl. No.: 13/996,366

(22) PCT Filed: Dec. 20, 2011

(86) PCT No.: PCT/JP2011/079530
§ 371 (c)(1),
(2), (4) Date: Feb. 6, 2014

(87) PCT Pub. No.: WO2012/086648
PCT Pub. Date: Jun. 28, 2012

(65) Prior Publication Data
US 2014/0138553 A1 May 22, 2014

(30) Foreign Application Priority Data
Dec. 21, 2010 (JP) .................. 2010-284571

(51) Int. Cl.
*A61B 6/00* (2006.01)
*G01T 1/17* (2006.01)
(Continued)

(52) U.S. Cl.
CPC ...... *G01T 1/17* (2013.01); *A61B 6/14* (2013.01); *A61B 6/4233* (2013.01); *G01T 1/2928* (2013.01); *A61B 6/0421* (2013.01); *A61B 6/4435* (2013.01); *A61B 6/4452* (2013.01)

(58) Field of Classification Search
CPC .......... G01V 5/00; G01V 5/04; G01V 5/104; G21K 2004/04; A61B 6/4435; A61B 6/4447; A61B 6/4233; A61B 6/4441; A61B 6/4452; G01T 1/1644; H01J 1/62; H01J 1/63
See application file for complete search history.

(56) References Cited

U.S. PATENT DOCUMENTS

| 5,744,806 A | 4/1998 | Fröjd |
| 2007/0071162 A1 | 3/2007 | Yamazaki |
| 2010/0127182 A1* | 5/2010 | Hackenschmied et al. ............ 250/370.09 |

FOREIGN PATENT DOCUMENTS

| JP | 11-511035 A | 9/1999 |
| JP | 2003-000587 A | 1/2003 |

(Continued)

OTHER PUBLICATIONS

International Preliminary Report on Patentability with annexes, mailed Apr. 10, 2013, and translation thereof.
(Continued)

*Primary Examiner* — Yara B Green
(74) *Attorney, Agent, or Firm* — Harness, Dickey & Pierce, P.L.C.

(57) ABSTRACT

An X-ray detector is provided with a plurality of modules each having a plurality of detection elements each composing a pixel, in which the detection elements convert incoming radiations to electric data depending on amounts of the radiations. The plural modules are mutually adjacently arranged on the same surface with a gap having a known width formed therebetween, such that the modules are arranged along at least one of a first X-axis and a first Y-axis, wherein the radiation detector is given a scan direction which is set along one of the first X- and Y-axes and the first Y-axis is perpendicular to the first X-axis. The plural detection elements of each module are two-dimensionally arranged along a second X-axis and a second Y-axis which are set obliquely to the first X-axis and the first Y-axis respectively and which are perpendicular to each other.

19 Claims, 25 Drawing Sheets

(51) Int. Cl.
*A61B 6/14* (2006.01)
*G01T 1/29* (2006.01)
*A61B 6/04* (2006.01)

(56) References Cited

FOREIGN PATENT DOCUMENTS

| JP | 2004-325183 | A | 11/2004 |
| JP | 2006-101926 | | 4/2006 |
| JP | 2007-117717 | A | 5/2007 |
| JP | 2008-298556 | A | 12/2008 |
| JP | 2010-125249 | A | 6/2010 |
| JP | 2010-243394 | A | 10/2010 |

OTHER PUBLICATIONS

International Search Report (English and Japanese) and Written Opinion of the ISA (Japanese) for PCT/JP2011/079530, ISA/JP, mailed Apr. 3, 2012.

\* cited by examiner

FIG.10
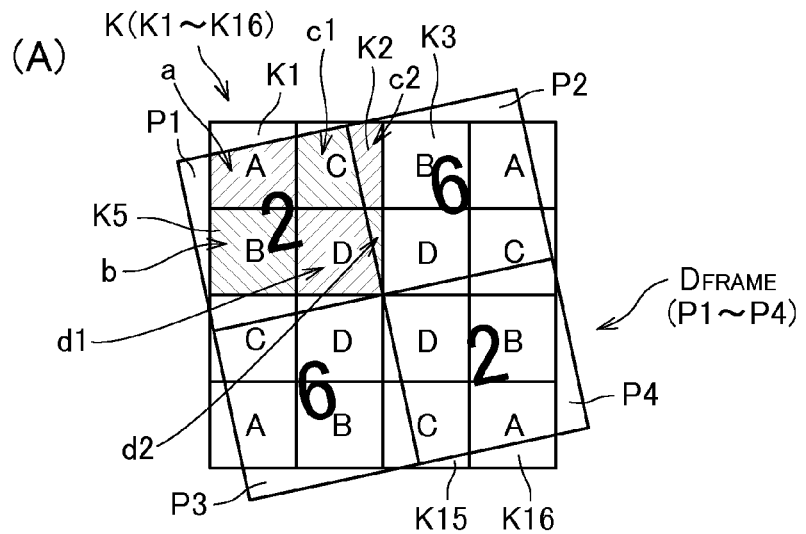
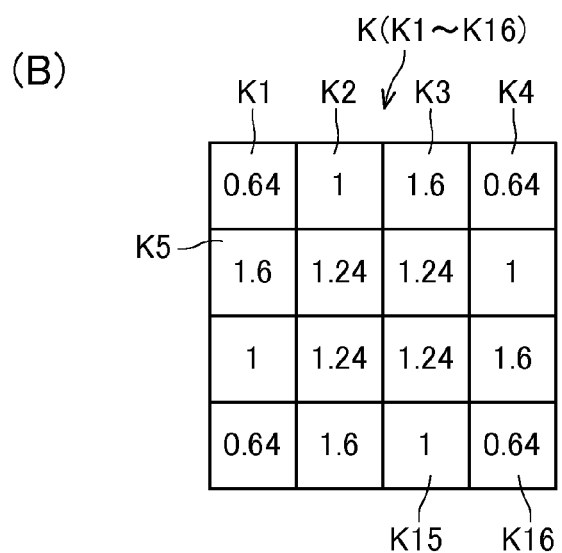

FIG.12
(A)
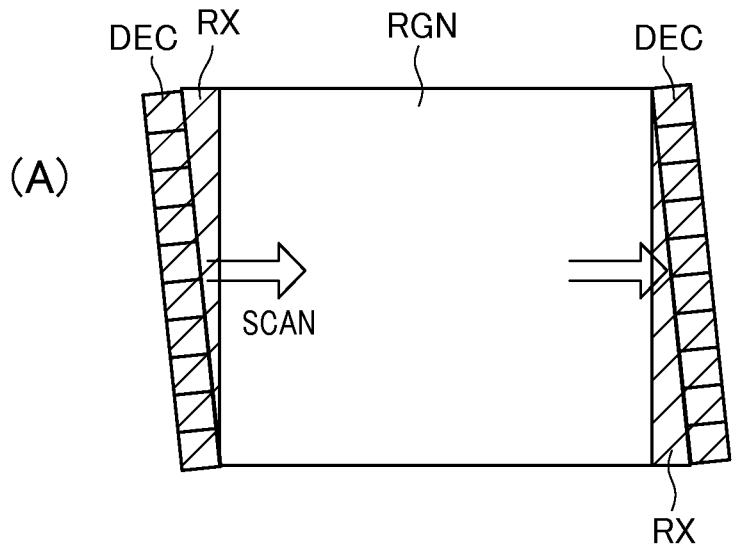
(CONVENTIONAL: SCAN BASED ON OBLIQUE ARRANGEMENT)
(B)
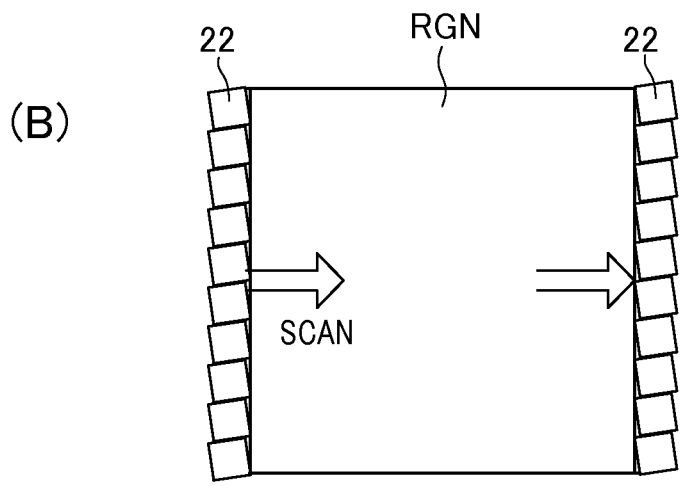
(THE PRESENT INVENTION: SCAN BASED ON OBLIQUE AND CASCADE ARRANGEMENT)

FIG.16
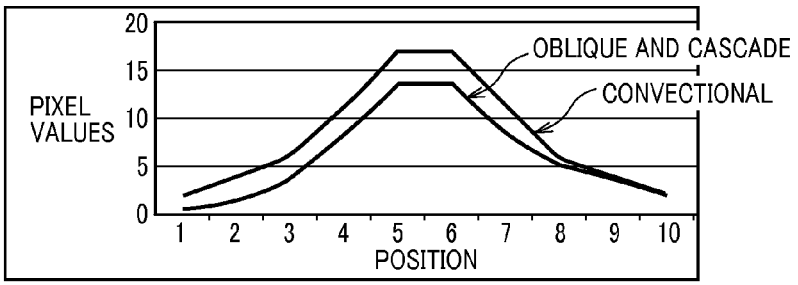
(A)
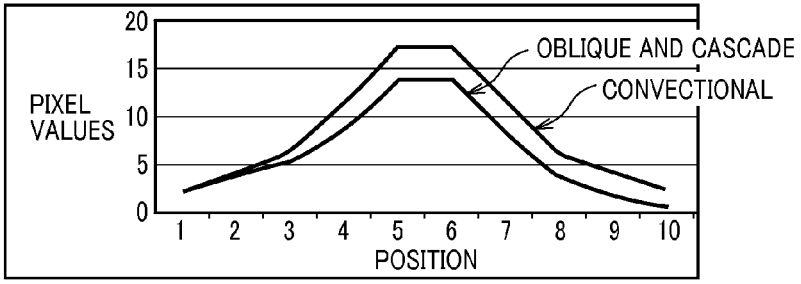
(B)
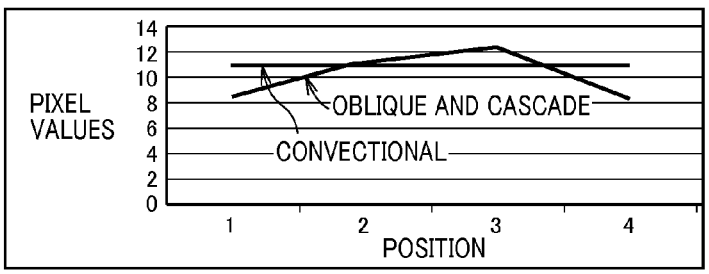
(C)
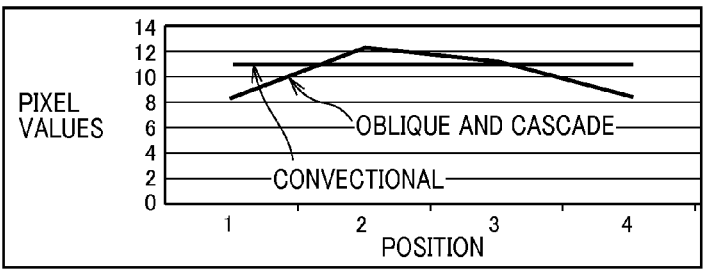
(D)

SCAN DIRECTION

RADIATION DETECTOR, AND RADIATION IMAGING APPARATUS PROVIDED WITH DETECTOR

CROSS-REFERENCE TO RELATED APPLICATIONS

This application is a 371 U.S. National Stage of International Application No. PCT/JP2011/079530, filed Dec. 20, 2011, which claims priority to Japanese Patent Application No. 2010-284571, filed Dec. 21, 201. The disclosures of the above applications are entirely incorporated by reference herein.

BACKGROUND OF THE INVENTION

1. Field of the Invention

The present invention relates to a radiation detector that detects quantities of radiation such as X-rays transmitted through an object being imaged and a radiation imaging apparatus provided with such a radiation detector to produce images of objects being imaged using data of the radiation detected by the detector, and in particular, to a radiation detector in which a plurality of direct conversion type of modules are arranged which have semiconductor layers to directly convert the radiation to electric signals corresponding in quantities to the radiation or a large-size radiation detector in which a plurality of indirect conversion type of modules are arranged and each module has detections cells which convert the radiation to light and then convert the light to electric signals, and a radiation imaging apparatus equipped with such a radiation detector.

2. Background Art

Techniques for medical modalities of recent years have been developed remarkably. Such medical modalities include medial panoramic imaging apparatuses which can acquire tomographic images along patient's tooth rows using X-ray beams and medical CT scanners which can acquire tomographic images along arbitrary sections at designated portions of patient's bodies.

No less important is the fact that performance improvement in X-ray detectors has contributed significantly to development of such X-ray-related medical modalities. As exemplified by a patent reference 1 for example, such X-ray detectors are known as, what is called, a direct-conversion type of X-ray detector with a semiconductor, in which the detector has a detection layer made of semiconductor such as CdTe so that X-ray beams impinging on this detection layer are directly converted to corresponding electric signals. Meanwhile, so called indirect conversion type X-ray detectors are also in frequent usage, in which the detectors have a scintillator, made of CsI and GOS, which convert radiation to light, and a CCD circuit, photo diode circuit or C-MOS circuit which converts the light to corresponding electric signals.

In these X-ray detectors, the X-ray detection layer of a semiconductor type detector is produced by making an ingot grow and forming and processing the grown ingot. Hence it is difficult to produce, as one element, a detector having a larger detection area. In consideration of this fact, modules of given sizes (for 8 mm×8 mm, which is rectangular) are produced where a given number of pixels (for example 40×40 pixels) are mapped in a two-dimensional array. A plurality of such modules are adjacently located closely with each other in a two-dimensional form or a liner form, so that a structure with adjacent arrangement of the modules is employed. This can provide an X-ray detector having a two- or one-dimensional detection area, in which, in fact, even the one-dimensional detection area still presents a detection width corresponding to one module. In this close arrangement of the modules, it is necessary to provide both high assembly accuracy and wiring spaces to the modules, which requires that there be arranged spaces of a given width between modules (this space is also called "a gap", of which the width is normally approximately 0.5-5 times that of a single pixel). From a viewpoint of producing compact detectors, these spaces result in dead space.

By the way, in panoramic imaging apparatuses and X-ray CT scanners, X-ray scanning is normally performed parallel with the direction of one of mutually orthogonal coordinate axes along which pixels of an X-ray detector are arranged longitudinally and laterally in the rectangular detection areal. For instance, the lateral axis of the orthogonal coordinate and the scan direction coincide with each other. In this case, there is a gap present between modules, which has a given width. The extending direction of the gap coincides with the scan direction. However, the X-ray detector is moved laterally for scanning, so that the gap acts as a dead zone which cannot pickup X-ray transmittance information of an object being examined.

In addition, the pixels of the X-ray detector include pixels located at the outermost ends of each module, where such outermost pixels tend to exhibit unstable X-ray detection performance. Hence, when X-ray transmission data (i.e., frame data) including data from pixels with no detection and data from pixels with unstable detection are used to reconstruct images, artifacts are caused in the images and/or image information is incomplete in the images, which will result in a reduction of accuracy of image interpretation.

To improve this issue, there have been known X-ray detectors which are disclosed by a patent reference 2 and a non-patent reference 1, in which the detectors have detection surfaces composed of plural rectangular modules arranged obliquely to the scan direction. In such detectors, the longitudinal direction of a gap located between modules, which acts as a dead space, is also oblique to the scan direction, whereby there is no dead zone which cannot detect data.

Additionally, in recent years, use of a photon counting type of X-ray detector has been started, as indicated by patent references 3, 4, and 5, and a non-patent reference 2.

PRIOR ART REFERENCES

Patent References

[Patent Reference 1] U.S. Pat. No. 5,952,646
[Patent Reference 2] JP-A-2010-125249
[Patent Reference 3] JP-A-2000-069369
[Patent Reference 4] JP-A-2004-325183
[Patent Reference 5] JP-A-2004-325183

Non-Patent References

[Non-Patent Reference 1]
Kazuhiko KIMURA et al., "Study of availability of quantum counting type of X-ray imaging in image diagnosis for disease of breast", NIPPON ACTA RAdiologica 1997; 57; 791-800
[Non-Patent Reference 2]
J. S. Iwanczyk, et al, "Photon Counting Energy Dispersive Detector Arrays for X-ray Imaging"; Nuclear Science Symposium Conference Record, 2007; NSS '07, IEEE

SUMMARY OF THE INVENTION

Issues to be Solved by the Invention

However, even if the detector whose detection area is rectangular and arranged obliquely to the scan direction is moved along the scan direction, that is, a "scan with oblique arrangement" is performed, according to the foregoing patent reference 2 and non-patent reference 2, an image is reconstructed based on an orthogonal-coordinate system detection area whose lateral axis is set to agree with the scan direction. As a result, in the scanned detection area, there is left partial areas which are not used for reconstructing an image, which partial areas are useless in terms of data acquisition. In addition, acquisition from such partial areas provides a patient with unnecessary X-ray exposure.

When the photon counting type of X-ray detector is produced by arranging a plurality of modules adjacently to each other, which is according to the foregoing patent reference 3, it is required to make as pixels on an ASIC layer, with signal processing circuits immediately under detection layers serving as pixels. The volume of the signal processing circuits becomes larger compared with that of a signal integration type of X-ray detector. This means that, in the photon counting type of detector, it is difficult to make each pixel smaller (down to a size of 150 µm or less) in structure as well as causing problems with performance and production cost, normally resulting in a pixel size of approx. 200 µm, which is a practical size. In other words, images reconstructed using data from the photon-counting type of detector are inferior in image resolution to those reconstructed using data from signal integration detectors whose pixels are approx. 100 µm in size. That is, fineness of images is poorer. Further, the former images are subjected to larger digital distortions, reducing accuracy in interpreting the images.

The present invention has been made in consideration of the foregoing various circumstances, and an object of the present invention is to provide a radiation detector provided with a plurality of modules mutually adjacently arranged, which is able to largely reduce the influence of dead zones on images to be produced, and to provide finer and higher-resolution images, while requiring lower radiation exposure. Another object is to provide finer and higher-resolution images by a radiation imaging apparatus provided with the foregoing radiation detector, which images can be represented in an analog and natural appearance and which apparatus is also able to largely reduce the influence of dead zones on images.

Means for Solving the Issues

In order to achieve the foregoing objects, the present invention provides as one of its modes a radiation detector provided with a plurality of modules each provided with a plurality of detection elements each composing a pixel, each of the detection elements converting, pixel by pixel, incoming radiation to electronic data whose magnitude corresponds to an intensity of the radiation. The radiation detector is characterized in that the plurality of modules are mutually adjacently arranged on the same surface with a gap having a known width formed therebetween, such that the modules are arranged along at least one of a first X-axis and a first Y-axis, wherein the radiation detector is given a scan direction which is set along one of the first X-axis and the first Y-axis and the first Y-axis is perpendicular to the first X-axis; and the plurality of detection elements of each of the modules are two-dimensionally arranged along a second X-axis and a second Y-axis which are set obliquely to the first X-axis and the first Y-axis respectively and which are perpendicular to each other.

Furthermore, as another mode, the present invention provides a radiation imaging apparatus, comprising: a radiation source; a radiation detector provided with a plurality of modules each provided with a plurality of detection elements each composing a pixel, each of the detection elements converting, pixel by pixel, incoming radiation from the radiation source to electronic data whose magnitude corresponds to an intensity of the radiation, the radiation detector regularly and repeatedly outputting, as frame data, the data outputted from the plurality of modules as frame data; and image producing means for producing the frame data as image data. The apparatus is characterized in that: the plurality of modules are mutually adjacently arranged on the same surface with a gap having a known width formed therebetween, such that the modules are arranged along at least one of a first X-axis and a first Y-axis, wherein the radiation detector is given a scan direction which is set along one of the first X-axis and the first Y-axis and the first Y-axis is perpendicular to the first X-axis; and the plurality of detection elements of each of the modules are two-dimensionally arranged along a second X-axis and a second Y-axis which are set obliquely to the first X-axis and the first Y-axis respectively and which are perpendicular to each other.

Effects of the Invention

In the radiation detector, such as an X-ray detector, configured with a mutually adjacent arrangement of plural modules, it is possible to greatly reduce influence of dead zones of the detector on image quality, while still suppressing an amount of radiation exposure. When this radiation detector is mounted on a radiation imaging apparatus, it is also possible to largely reduce influence of dead zones of the detector on image quality, suppress radiation exposure amount, and provide higher-resolution and finer images having an analog and natural appearance.

BRIEF DESCRIPTION OF THE DRAWINGS

In the accompanying drawings:

FIG. 10 provides diagrams explaining the sub-pixel technique based on area ratios;

FIG. 12 provides diagrams explaining a difference between a scan performed based on an oblique cascaded arrangement of modules according to the present invention and a scan performed based on an oblique arrangement of modules according to the conventional technique;

FIG. 16 provides graphs each showing, together with comparison with conventional examples, simulation of a profile of each of pixel-value lines along the plural lines indicated in FIG. 15;

DETAILED DESCRIPTION OF PREFERRED EMBODIMENTS

With reference to the accompanying drawings, embodiments of a radiation detector according to the present invention will now be described.

First Embodiment

Referring to FIGS. 1-17, a first embodiment of the radiation detector according to the present invention will now be described.

In the present embodiment, the radiation detector according to the present invention is an X-ray detector adopted by a dental X-ray panoramic imaging apparatus (hereinafter simply referred to as a panoramic imaging apparatus). Of course, as described later, this radiation detector can be mounted in a medical X-ray CT (Computed Tomography) scanner and an industrial X-ray CT apparatus. The X-ray detector in the present embodiment is exemplified as a photon counting type of X-ray detector. However, the radiation detector according to the present invention will not always be limited to the photon counting type, but may be applied to an integration type of detector which has the capability of detecting an intensity of incoming X-rays as an integrated amount calculated every designated period.

Figure 1:
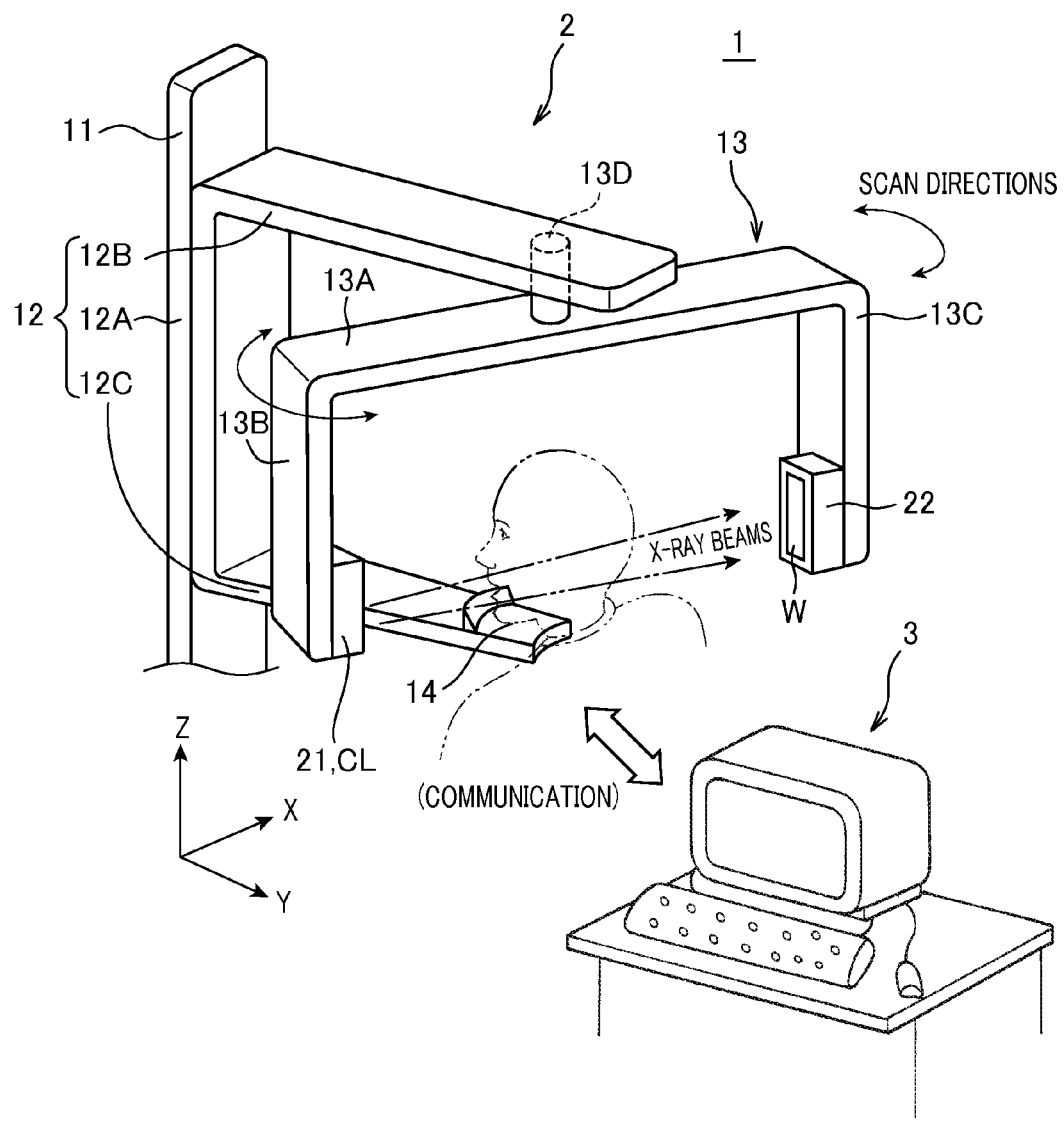
FIG. 1 is a diagram outlining a dental panoramic imaging apparatus in which a radiation imaging apparatus and a radiation detector, which are according to a first embodiment of the present invention, are reduced into practice.

FIG. 1 outlines the panoramic imaging apparatus 1. This panoramic imaging apparatus 1 is provided with a gantry (data acquiring system) which acquires data from a patient P being examined, and a console 3 which controls operations of the gantry 2 and produces images and other information by processing the acquired data.

The gantry 2 includes a pillar 11. The lengthwise direction along which the pillar extends is referred as a longitudinal direction (or a vertical direction: a Z-axis direction) and a direction orthogonal to the longitudinal direction is referred to as lateral directions (i.e., directions along an X-Y plane). The pillar 11 is provided with a vertically moved arm unit 12, which is approximately formed into a laterally-facing U-shape and movable longitudinally. The vertically moved arm unit 12 includes a longitudinal arm 12A movable along the pillar 11 and an upper lateral arm 12B and a lower lateral arm 12C which extends laterally from the upper and lower ends of the longitudinal arm 12A respectively. At a given position of the upper lateral arm 12B, there is provided a rotation arm unit 13 which is rotatable along the X-Y plane. An end portion of the lower lateral arm 12C is configured as a chin rest 14 on which the chin of a patient P is laid. For imaging, as shown by a two-dot chain line in the figure, the patient P lays his or her chin on the end portion. The longitudinal position of the vertically moved arm unit 12 can be adjusted by a not-shown drive mechanism, depending on the height of the patient P.

The rotation arm unit 13, which is formed into an approximate downward U-shape, includes a lateral unit 13A and a source-side vertical arm 13B and a detector-side vertical arm 13C which extend downward from the ends of the lateral arm 13A respectively. The lateral arm 13A is suspended by a rotation shaft 13D and rotated in both directions on the rotation shaft 13D by a not-shown drive mechanism such as an electric motor or other mechanism. At a lower end portion of the source-side arm 13B, an X-ray tube 21 is arranged. The X-ray tube 21 radiates, for example, pulsed X-rays, and the radiated X-rays are collimated by a collimator CL to be transmitted to the detector-side vertical arm 13C through the chin of the patient P (refer to two-dot chain lines). Meanwhile, at the lower end portion of the detector-side vertical arm 13C, an X-ray detector 22 (herein referred to as a detector) is arranged which has an X-ray incidence window W (for example, 6.4 mm in width×150 mm in height). Incidentally the collimator CL has a slit for the above collimation, and the slit is formed to enable the size of a collimated fan beam to equal the X-ray incidence window W or become slightly (for example 1 mm) larger than the incidence window W.

The detector 22 is formed as a photon counting type of X-ray detector employing a semiconductor layer that directly converts incoming radiation beams to electric signals, that is, employing a direct conversion system. A laminated structure adopted by this detector 22 will be detailed later using FIG. 6, while a relationship between the semiconductor layer and pixels will now explained here.

In this photon counting type of detector 22, the semiconductor layer has a surface onto which X-rays are incident, and on this surface, there is formed a common electrode which is called a charging electrode, to which a higher voltage such as −500 V is applied. On the other surface of the semiconductor layer, there are formed collecting electrodes, which are two-dimensionally arrayed and correspond to pixels. Hence, this two-dimensional arrangement of the collecting electrodes gives the semiconductor layer a structure equivalent to a two-dimensional array of X-ray detecting elements. In this embodiment, these X-ray detecting element portions, which substantially function as pixels, are referred to as detection elements S (refer to FIG. 3).

The detector 22 thus has two-dimensionally arrayed detection elements S, that is, pixels (the number of pixels is for example 32×750 pixels). The size of each pixel is for example 200 μm×200 μm, and this pixel size is made to be sufficiently smaller, which makes it possible to detect the X-rays as a gathering of photons (having a property of particles). In the present embodiment, "the size which makes it possible to detect the X-rays t as a gathering of their photons" is defined as "a size which makes it possible to substantially ignore occurrence of a pileup phenomenon among pulse signals responding to each particle incidence or which makes it possible to estimate amounts of the pileups, when a plurality of particles of the radiations (e.g. X-rays) arrive sequentially at the same pixel position or therearound". When the pileup phenomenon occurs, there occurs a loss of count of the number of X-ray particles in a characteristic showing "the incidence number vs. the actual measurement number" of X-ray particles. With consideration of this fact, the collecting pixels of the X-ray detector 22 have a size which can prevent the counting loss or regard that there occurs substantially no counting loss, or have a size which can estimate amounts of the counting loss.

The detector 22 is not always limited to be produced as the direct conversion type and photon counting type of detector which uses semiconductors, but may be produced as other types of detectors. For example, the detector may be produced by combining a scintillator and an optical detector. Further, how to process signals in the detector is not limited to the photon counting type, and a detector with a signal processing circuit referred to as an integration type may be employed.

All the pixels of the detector 22 therefore count in number photons of incident X-rays and output electrical frame data which show the counts. The object P being examined stands at a predetermined imaging position and, with the chin portion on the chin rest 14, the rotation arm unit 13 is driven to rotate therearound. During the rotation, an X-ray beam is radiated at intervals or continuously, while the X-ray beams are detected by the detector 22 as frame data at a higher frame data of, for example, 300 fps.

Figure 2:
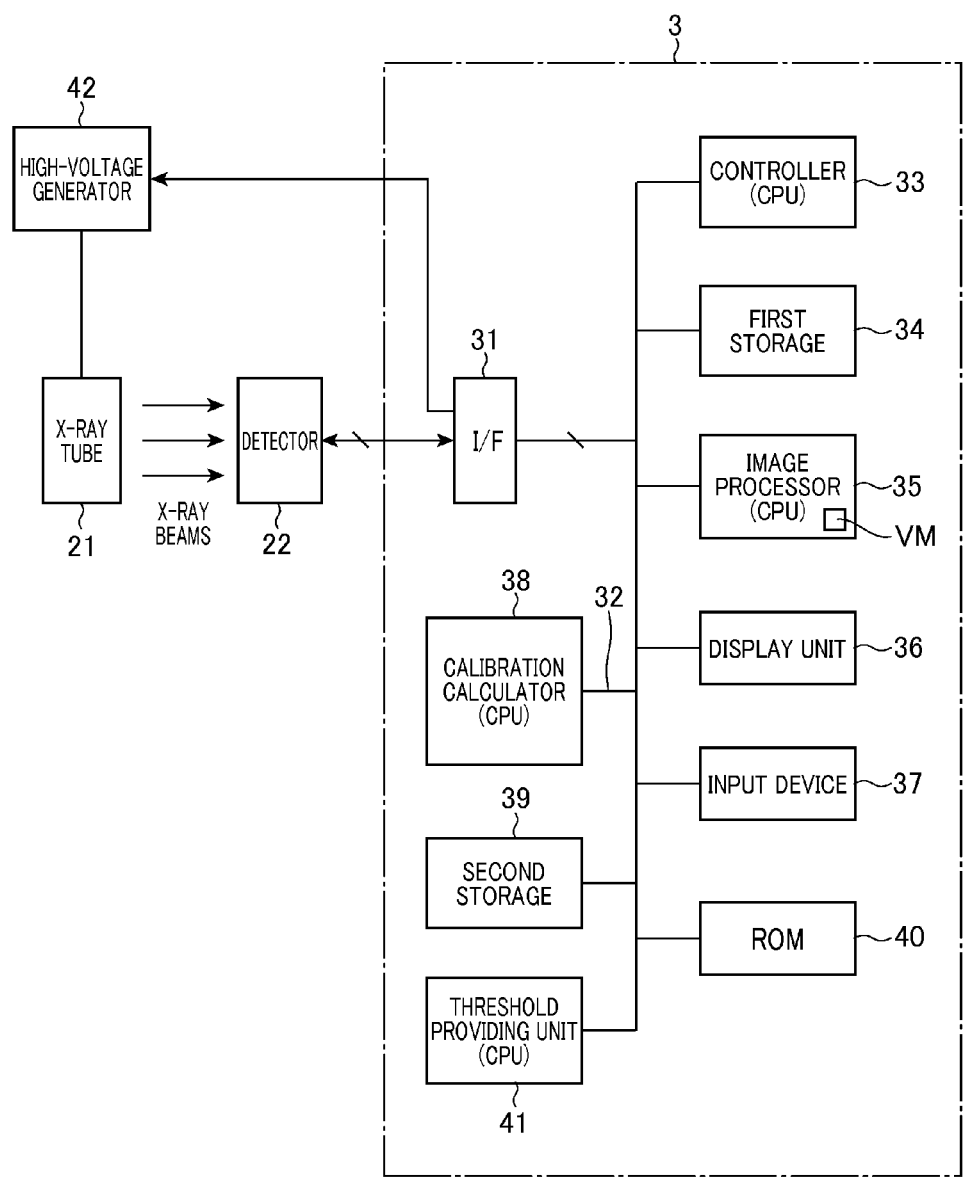
FIG. 2 is a block diagram outlining an electric configuration of the panoramic imaging apparatus.

As shown in FIG. 2, the console 3 is provided with an interface 31 (I/F) for relaying input and output of signals, and this interface 31 is communicably connected to, via a bus 32, a controller 33, a first storage 34, an image processor 35, a display unit 36, an input device 37, a calibration calculator 38, a second storage 39, a ROM 40, and a threshold providing unit 41.

The controller 33 has a CPU (central processing unit) and this CPU controls drive of the gantry 2 according to a program previously stored in the ROM 40. This control includes output of a command value to the high-voltage generator 42 which supplies a high voltage to the X-ray tube 21, a drive command to the image processor 35, and a drive command to the calibration calculator 38. The first storage 34 stores frame data transmitted from the gantry 2 via the interface 31.

The image processor 35 is a computer provided with a CPU. This image processor 35 starts to operate based on a program previously stored in the ROM 40 by responding to a processing start command from the controller 33. In this operation, the frame data stored in the first storage 34 is processed on a known tomosynthesis method whose main part is calculation for a shift and add technique, thus providing an X-ray transmission image of the tooth row in the oral portion of the object P. The display unit 36 is provided for displaying produced X-ray transmission images, information showing operations of the gantry 2, and operator's operation information given using the input device 37. The input device 37 is used by an operator to provide the system with information necessary for the imaging.

The calibration calculator 38 operates in response to a drive command from the controller 33. The ROM 40 stores a program needed to operate the calibration calculator 38. This calibration calculator 38 is in charge of calibrating thresholds for energy discrimination, where the thresholds are given every pixel and every energy discriminating system to each pixel in a data acquisition circuit described later. The second storage 39 stores the values of thresholds produced, by the calibration, every pixel, every energy discriminating system, and every energy amount. The thresholds are read when performing imaging and supplied to the data acquisition circuit later described.

The controller 33, the image processor 35, the calibration calculator 38, and the threshold providing unit 41 all are provided with CPUs operating under programs previously given in the ROM 40.

The foregoing detector 22 will now be detailed. The electric configuration of the detector 22 will be first described in terms its entire configuration, and an aggregation of plural detection elements S called a module will be described, where a configuration unit for assembly is structurally detailed and how to assembly the modules is also described.

(Electric Entire Configuration of Detector)

Figure 3:
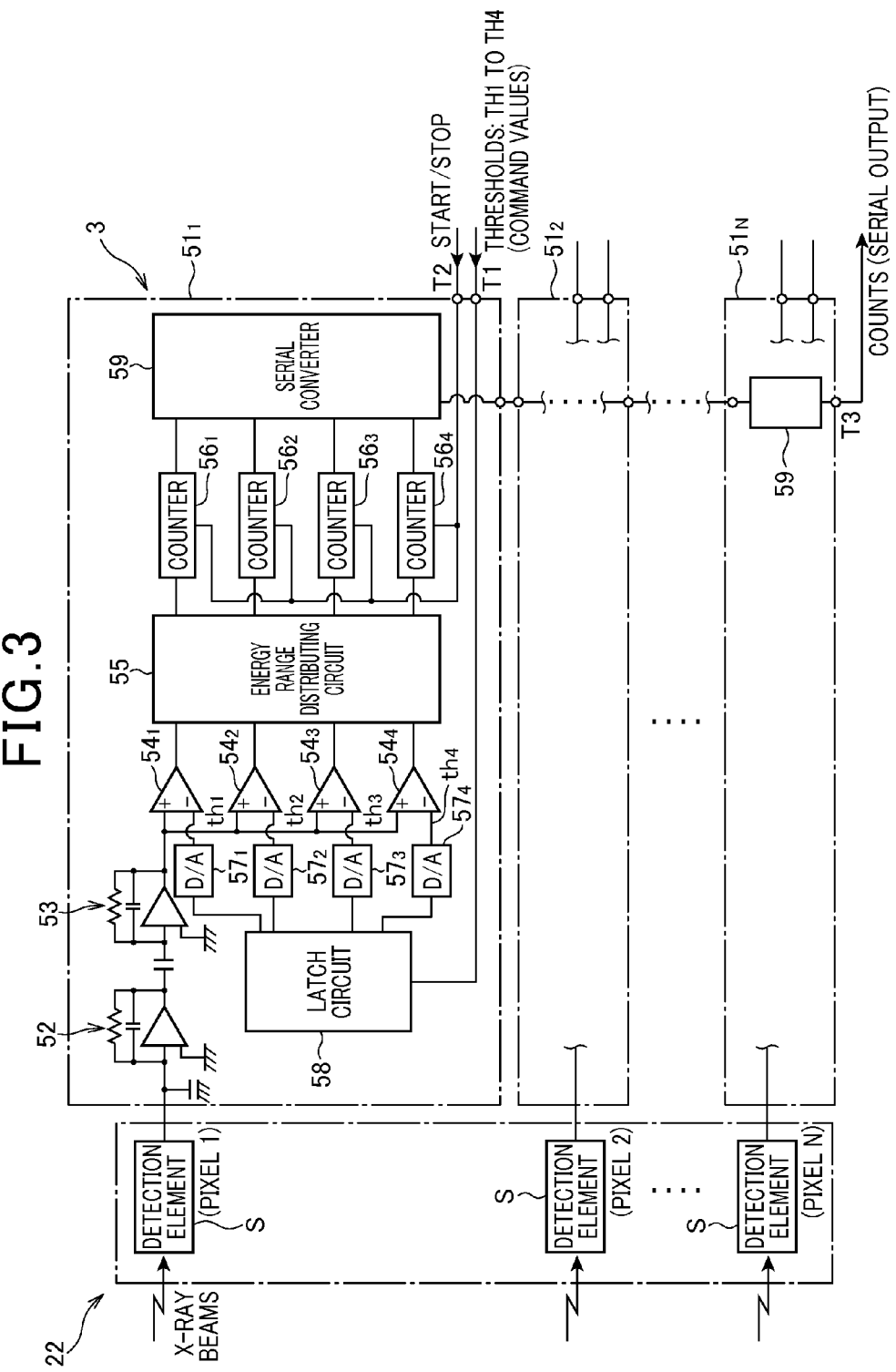
FIG. 3 is a block diagram outlining an electric configuration of a detector used by the panoramic imaging apparatus.

First, FIG. 3 will be referred to describe the overall electric configuration of the detector 22.

The detector 22 has the X-ray incidence surface in which, as described, there is provided a two-dimensional array of the detection elements S respectively composing the pixels. Each detection element S detects an X-ray beam incoming to this detection element and outputs pulsed electric signals depending on amounts of its X-ray energy. To process these electric signals, there are data acquisition circuits $51n$ (n=1–N: N=the number of all pixels=the number of all acquisition channels) on the output side of the respective detection elements S.

Each of the data acquisition circuits $51n$ (n=1 to N) has a charge amplifier 52 receiving an analog electric signal outputted from a corresponding detection element S. On the output side of each charge amplifier 52, there are provided a waveform shaping circuit 53, multiple-stage comparators $54_1$ to $54_t$ (in this example t=4), an energy range distribution circuit 55, multiple-stage counters $56_1$ to $56_t$ (in this example, t=4), multiple-stage D/A converters $57_1$ to $57_4$ (in this example, t=4), a latch circuit 58, and a serial converter 59.

The charge amplifier 52 is connected to the collecting electrode of each detection element S, whereby an electric charge collected in response to the incidence of an X-ray particle is collected to be output as an electric pulse signal. The output of this charge amplifier 52 is connected to the waveform shaping circuit 53 whose gain and offset are adjustable, so that the detected pulse signal is subjected to waveform shaping under a pre-adjusted gain and offset. The gain and offset of this waveform shaping circuit 53 are adjusted by calibration in view of both irregularities in an electric-charge charging characteristic and irregularities in a circuit characteristic of each pixel composed of the detection element S.

The output of the waveform shaping circuit 53 is connected to the comparison input terminals of the plural comparator $54_1$-$54_4$. Mutually different values of analog thresholds $th_1$-$th_t$ (in this example, t=4) are applied to the reference input terminals of the plural comparator $54_1$-$54_4$ respectively. Hence, one pulse signal can be compared with the different thresholds $th_1$-$th_4$. This comparison is for checking (discriminating) an amount of energy of an incident X-ray particle to allocate the energy into one of previously divided energy ranges. Depending on which one of the thresholds $th_1$-$th_4$, the height of a pulse signal exceeds (that is, the height shows an amount of energy of each incident X-ray particle), an energy range can be discriminated from other ranges. The lowest threshold $th_1$ is set to avoid detection of disturbances, noise due to circuitry including the detection element S and the charge amplifier 42, and lower energy radiation which is unnecessary for imaging. Incidentally the number of thresholds, i.e., the number of comparators, is not necessarily limited to four, but may be any number of two or more including a threshold for the foregoing thresholds $th_1$.

The foregoing thresholds $th_1$-$th_4$ are practically given, every pixel, that is, every collection channel, as digital values, through the interface 32 from the calibration calculator 38 of the console 3. The reference input terminals of the comparator $54_1$-$54_4$ are connected to the output terminals of the four D/A converters $57_1$-$57_4$ respectively. The D/A converters $57_1$-$57_4$ are connected to a threshold reception terminal $T_1$ (–$T_N$) via the latch circuit 58, and this threshold reception terminal $T_1$ (–$T_N$) is connected to the interface 32 of the console 3.

The latch circuit 58 is configured to latch the digital thresholds $th_1$-$th_4$ provided via the interface 31 and the threshold reception terminal $T_1$ (–$T_N$) from the threshold providing unit 40, and output the latched values to the corresponding D/A converters $57_1$-$57_4$. Hence, the D/A converters $57_1$-$57_4$ are able to provide the analog thresholds $th_1$-$th_4$, which are commands, to the comparators $54_1$-$54_4$ as voltage values.

The output terminals of the comparators $54_1$-$54_4$ are connected to the energy range distribution circuit 55, as shown in FIG. 3. This circuit 55 is configured to interpret outputs of the plural comparators 541-544, in other words, compares results of a pulse voltage corresponding to an amount of energy of a detected X-ray photon with the threshold th1 (–th4), and then allocates the energy to one of energy ranges 1-4.

Each of the counters 561-564 is configured to count every time when a pulse signal is given from the energy range distribution circuit 55. Each counter thus measures, as a value accumulated during a given period of time periodically repeated every given period, the number of X-ray photons whose energy has been discriminated into the energy range assigned to this counter. To the counters 561-564, start and stop signals are given from the controller 33 of the console 3 via a start/stop terminal T2. Measurement of the given period of time is managed using a reset circuit owned by the counter itself.

In this way, during the given period of time lasting until a reset, the number of X-ray particles incoming to the detector 12 is measured by the plural counters $56_1$-$56_4$ every pixel and every energy range. The measurements of the number of X-ray particles are parallely outputted, as digital measurement data, from the respective counters $56_1$-$56_4$, and then converted into serial format data by the serial converter 59. All the serial converters 59 for all the channels (i.e., collecting pixels) are connected serially to each other. Thus, the measurements are outputted as serial digital measurement data from the serial converter 59 of the last channel and the measurement data are transmitted to the consol 3 via an output terminal T3. In the console 3, the interface 31 receives the measurement data to store the data in the first storage 34.

The image processor 35 reads the measurement data stored in the first storage 34 in response to an operator's command received from the input device 36. Using the read measurement data, the image processor 35 reconstructs an image, e.g. an X-ray transmission image of a cross section along the tooth row (panoramic image) according to the tomosynthesis method. This panoramic image is displayed such as on a display unit 46.

(Structure of Detector and Mounting Method)

Hereinafter, the configuration of the detector 22 is described, the detector 22 being configured by packaged unit devices which are called modules.

Figure 4:
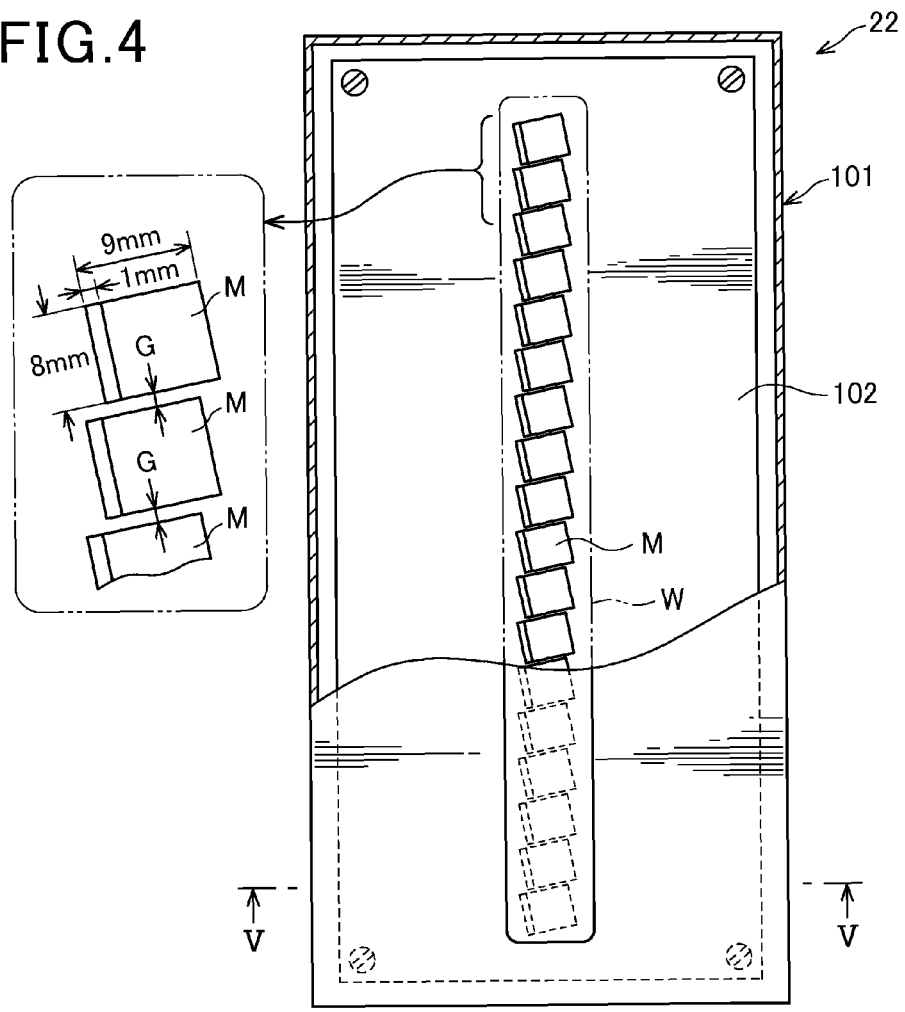
FIG. 4 is a plan view showing the detector whose X-ray incidence-side outer surface is partly broken and whose partial view is enlarged.
Figure 5:
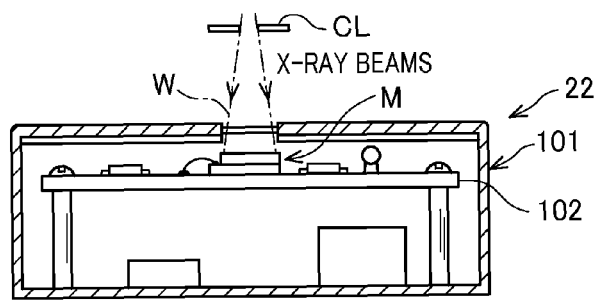
FIG. 5 is a sectional view outlined along a V-V line in FIG. 4.

The detector 22 has an appearance as shown in FIGS. 4 and 5. As shown in these figures, the detector 22 is in a rectangular shape and has a lunchbox-shaped housing 101 having a given height. Necessary components are incorporated in the housing 101. The components include a motherboard 102. The housing 101 is formed with a rectangular X-ray incidence window W made of a carbon material or the like. Right beneath the incidence window W, an arrayed structure of modules is located.

Specifically, on the motherboard 102, or right beneath the X-ray incidence window W, a plurality of modules M each having a group of unit elements (i.e. detection elements S) are mounted to directly convert incoming X-rays into electric pulse signals on a pixel basis. Each module M is a manufacturable unit that is a packaged unit device having a two-dimensionally arrayed plurality of detection elements S. The plurality of modules M are arranged being adjacent to each other on the motherboard 102 with a gap of a known width being given therebetween to configure a group of detection elements S needed to the detector 22.

Figure 6:
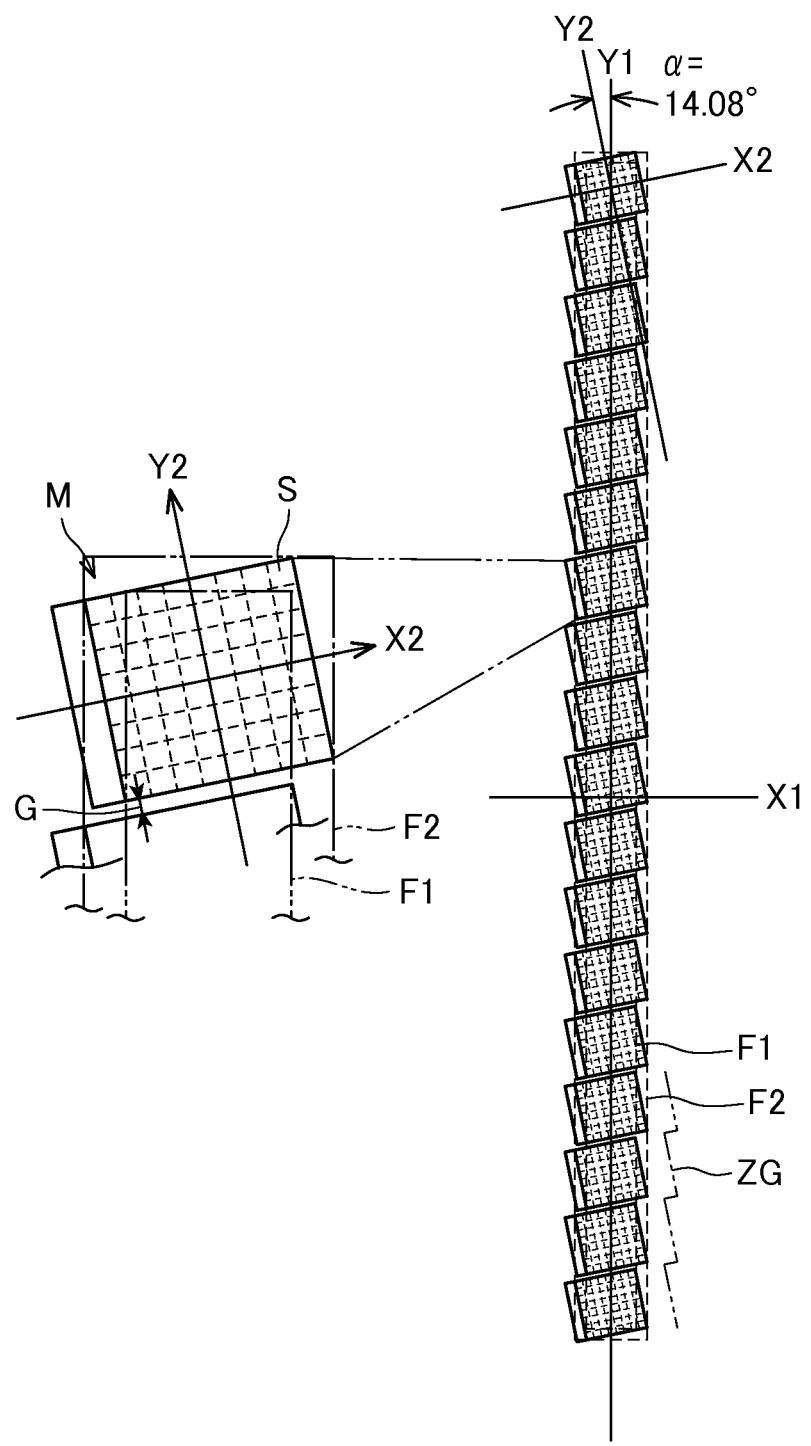
FIG. 6 is a view explaining arrangement of modules in the detector.

As shown in FIG. 4, each module M has a plate-like structure in a rectangular shape with a size, for example, of 8 mm×9 mm. In the 8 mm×9 mm size plane, 1 mm plane corresponds to a lead. Accordingly, the plane forming a detection surface is a square of 8 mm×8 mm size. As shown in FIG. 6, in the 8 mm×8 mm square area, 40×40 pixels (i.e. detection elements S) are two-dimensionally and densely arrayed in a matrix in an orthogonal-coordinate system (second orthogonal-coordinate system) composed of a second X-axis X2 and a second Y-axis Y2.

Figure 7:
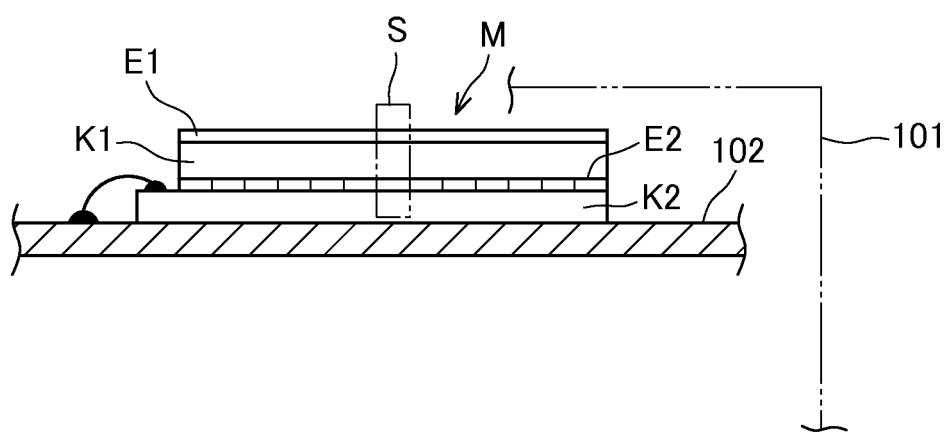
FIG. 7 is a side view outlining a side surface of one of the modules in the detector.

As shown in FIG. 7, each module M is configured being stacked, from an X-ray entry side, with a layer of common charging electrode E1, a detection layer K1 formed of a semiconductor, a layer of collecting electrodes E2 corresponding to respective pixels, and an ASIC (application specific integrated circuit) layer K2 in this order.

For example, the charging electrode E1 is applied with a comparatively high voltage of about several tens of minus (−) volts to several hundreds of minus (−) volts. The detection layer K1 is formed into a layer using a semiconductor material, such as a cadmium telluride semiconductor (CdTe semiconductor), a cadmium-zinc-telluride semiconductor (CdZnTe semiconductor) or a silicon semiconductor (Si semiconductor). The collecting electrodes E2 are in a grid pattern of a predetermined size to configure detection pixels. The size of this is 200 μm×200 μm, for example, i.e. the "size that can detect an X-ray as its particle". This enables counting of the number of photons (photon counting).

The X-ray photons incident on the detection circuit K1 generate pairs of electron and hole inside the layer and the electrons are collected to the collecting electrodes E2 having relatively positive potential. The electric charges derived from the electrons are detected as pulsed electric signals by the collecting electrodes E2. In other words, the X-rays that are incident on the detector 22 are directly converted to electric pulse signals.

The ASIC layer K2 is stacked onto the motherboard 102 so as to be connected to the plurality of collecting electrodes E2 via solder joints (not shown). The foregoing plurality of data acquisition circuits 51n (n=1 to N) are each formed and incorporated into the ASIC layer K2 for the corresponding one of the collecting electrodes E2 of the detection layer K1, i.e. for the corresponding one of the detection pixels.

The detection signals of each module M, i.e. the electric pulse signals corresponding to the "40×40" pixels, are outputted from the serial converters 59 of the respective detection pixels, the serial converters 59 being formed and incorporated into the ASIC layer K2. The electric pulse signals are serially collected using a circuit on the motherboard 102 and outputted from the output terminal T3 as shown in FIG. 3.

Referring to FIG. 6, an example of an arrangement of the modules M is described. The arrangement of the plurality of modules M is the most important feature of the present invention.

FIG. 6 shows two orthogonal-coordinate systems mentioned above. One orthogonal-coordinate system, or a first orthogonal-coordinate system, is composed of a first X-axis X1 and a first Y-axis Y1 perpendicular to the first X-axis. The other orthogonal-coordinate system, or a second orthogonal-coordinate system, is composed of a second X-axis X2 and a Y-axis Y2 perpendicular to the first X-axis. For example, the direction of the first X-axis X1 is permitted to coincide with the direction in which the paired detector 22 and the X-ray tube 21 are rotated about the object being examined P in performing X-ray panoramic imaging.

As shown in FIG. 6, as an example, the second orthogonal-coordinate system, i.e. the second X-axis X2 and the second Y-axis Y2, is slanted upward to the right by $\alpha=14.08°$ with reference to the first orthogonal-coordinate system, i.e. the first X-axis X1 and the first Y-axis Y1. As a matter of course, the slant $\alpha$ refers to a relative slant between the first and second orthogonal-coordinate systems. The second orthogonal-coordinate system may alternatively be slanted upward to the left by 14.08° with reference to the first X-axis X1 and the first Y-axis Y1. Taking account of errors in manufacture or mounting, the angle $\alpha$ of 14.08° may substantially be 14°. This oblique angle $\alpha$ is not necessarily limited to 14.08° but may be any oblique angle that falls in a given oblique range. The range of the oblique angle $\alpha$ may, for example, be 6° to 20.7° as will be described later.

In the second orthogonal-coordinate system among the two orthogonal-coordinate systems, the plurality of pixels, i.e. the plurality of detection elements S, of each of the plurality of modules M are two-dimensionally arrayed on a single plane so as to go along the second X-axis X2 and the second Y-axis Y2. In contrast, the plurality of modules M are arranged along the first orthogonal-coordinate system. In the example shown in FIGS. 4 to 6, the modules M are aligned in the longitudinal direction along the first Y-axis Y1, being adjacent to each other, with a gap G having a specified width being provided between the modules (see FIGS. 4 and 6).

The width of the gap G, if it is a known width, may be of any value. Nevertheless, from the standpoint of reducing calculation loads in processing the collected frame data, the width of the gap G may preferably be an integral multiple of 1/N (N is an integer of two or more) of the size of each pixel configured by the detection elements S. The width of the gap G is larger than ½, ⅓, ¼, ... of the size of a pixel by a factor of one, two, three, etc. As an example, when the size of a pixel is 200 μm, the gap G may be 100 μm, 200 μm, 300 μm .... The maximum value of the width of the gap G may preferably be set to a critical value that can prevent the occurrence of dead zones, in which no pixel data is collected from the object being examined, in a scan due to an excessive separation between the modules M that are obliquely adjacent to each other.

The plurality of modules M are obliquely arranged and mounted (with respect to the first orthogonal-coordinate system) in cascade (along the first Y-axis Y1) on the motherboard 102. Resultantly, the orthogonally arranged pixels of each module M are also obliquely arrayed with respect to the first X-axis X1 and the first Y-axis Y1. As a result, as show in FIG. 6, the "40×40" number of square pixels (detection elements S), each being 200×200 μm, forming a pixel group (module M) are densely arranged in the longitudinal direction along the first Y-axis Y1. In this case, each pixel group is arranged being slanted by 14.08° with respect to the first X-axis X1 and the first Y-axis Y1. In other words, the pixels corresponding to "40×number of modules M" are arranged in a zigzag pattern ZG (see FIG. 6) along the first Y-axis Y1.

Thus, as shown in FIG. 6, the plurality of modules M, each being in an identical square shape, are arranged along the first Y-axis Y1. Accordingly, the detection surface for the X-rays, which is formed by the entire modules M, is similarly in a zigzag pattern that is oblong along the first Y-axis Y1. For the detection surface in the zigzag pattern ZG, a field of view F1 is virtually set for coordinate conversion that will be described later. In the present embodiment, the field of view F1 is in a rectangle shape that internally contacts the corner portions of the square of each module M. However, the field of view F1 is not necessarily limited to the internally contacting area but may be a rectangular field of view F2 externally contacting the corner portions of each square (see FIG. 6). In some cases, a rectangular field of view larger than the externally contacting rectangle field of view F2 may be used.

(Processes of Signal Collection and Image Reconstruction)

Figure 8:
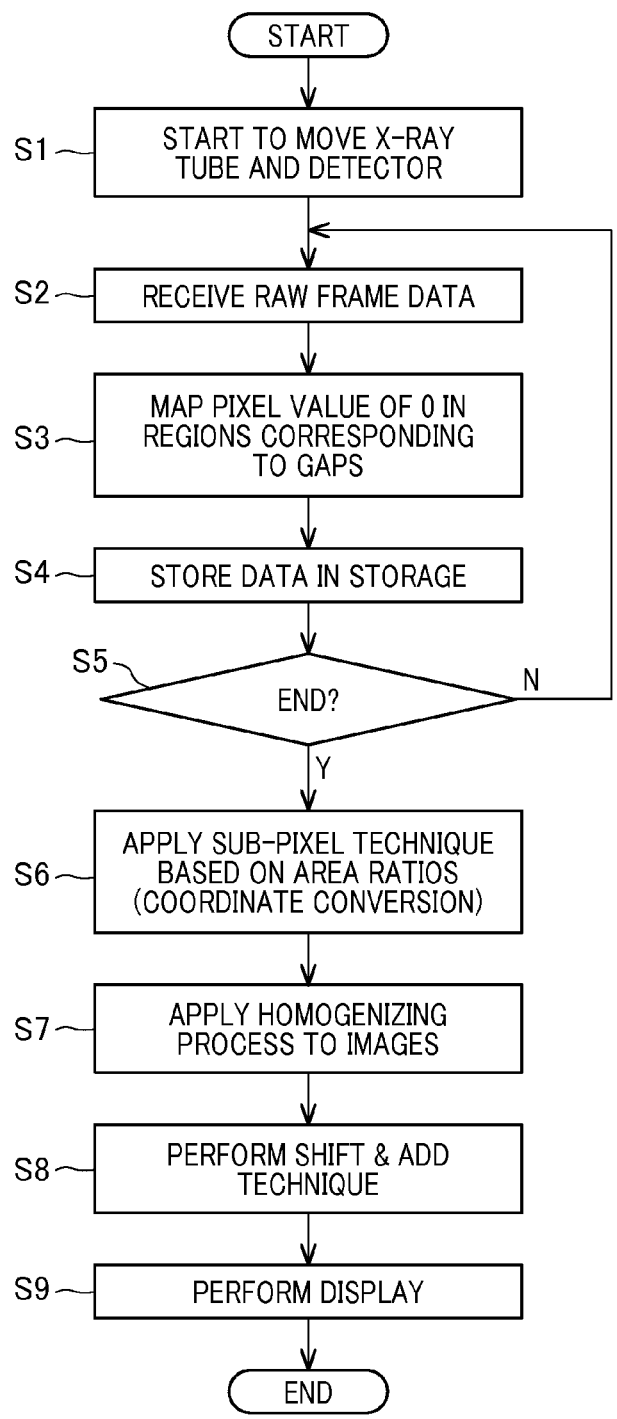
FIG. 8 is a flowchart outlining a process for data acquisition to image production, which is performed in the panoramic imaging apparatus.
Figure 9:
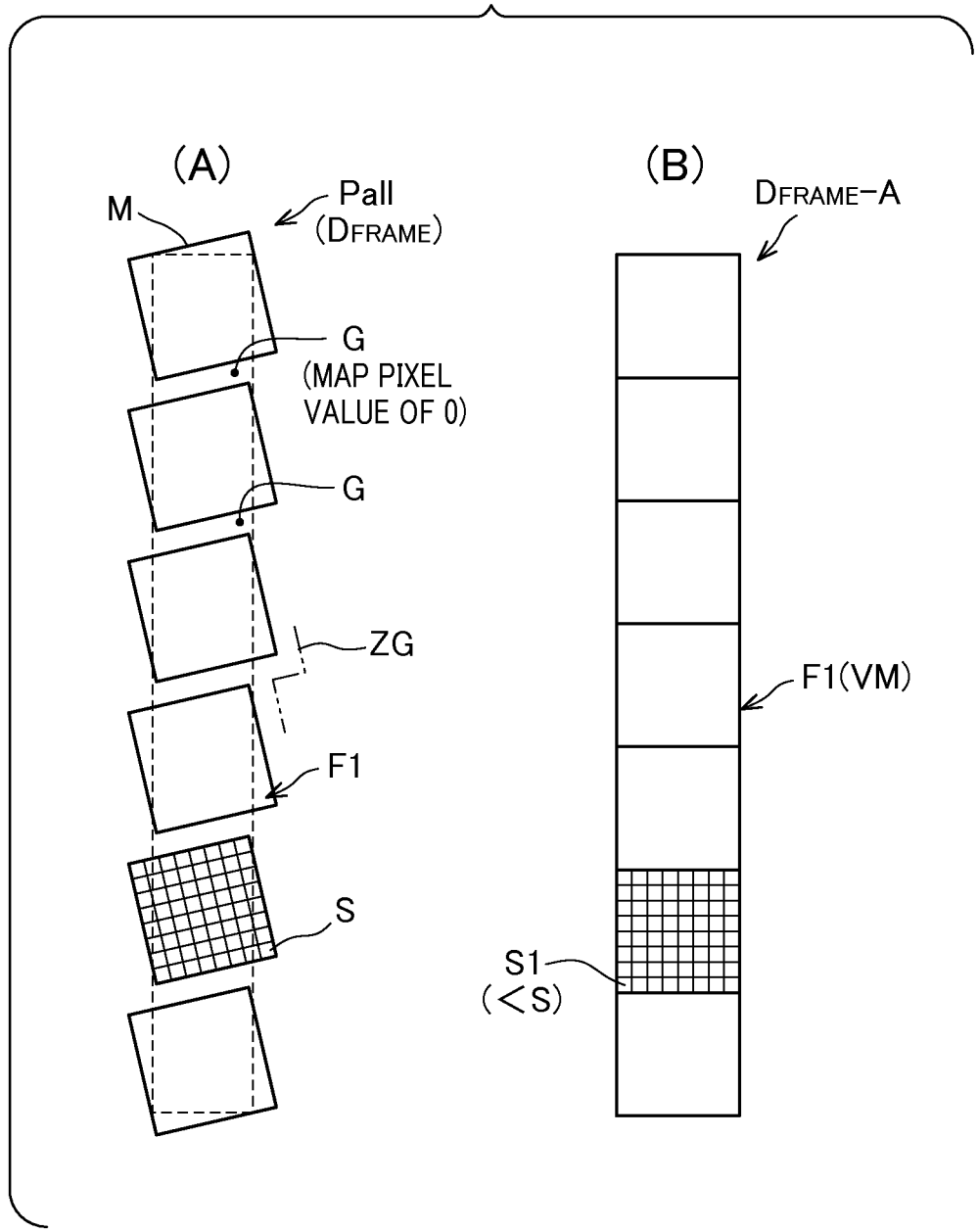
FIG. 9 provides diagrams showing modules used for performing a sub-pixel technique based on area ratios, pixels of the modules, and a positional relationship of virtual memory spaces.

Referring now to FIG. 8, hereinafter are described processes of signal collection and image reconstruction that are cooperatively performed by the controller 33 and the image processor 35 of the console 3.

When the X-ray panoramic imaging apparatus commands start of the panoramic imaging, the controller 33 of the control 3 gives an instruction, at step S1, to the paired X-ray tube 21 and the detector 22 to rotate about the chin portion of the object being examined P. At the same time, the console 3 instructs the X-ray tube 21 to radiate X-rays in accordance with a predetermined sequence. Thus, while the X-ray tube 21 and the detector 22 are in rotation, a pulsed X-ray, for example, is radiated from the X-ray tube 21 at every predetermined timing. Every time an X-ray is radiated, the X-ray transmits through the chin portion of the object being examined P and falls on the detector 22. In the detector 22, in response to the X-ray that has fell thereon, each of the plurality of modules M outputs digital electric pixel data on a pixel basis, the data reflecting the number of photons of the incident X-ray.

At step S2, as schematically shown in FIG. 9(A), the image processor 35 of the console 3 receives a rectangular frame data $D_{FRAME}$ in the zigzag pattern ZG, via the interface 31, from a detection surface Pall which is formed of the pixel data and formed of the plurality of modules M as a whole. The frame data $D_{FRAME}$ is temporarily stored in an internal memory of the image processor 35.

In the frame data $D_{FRAME}$, slit-like areas corresponding to the gaps G include no detection element S and hence no image data are present. Therefore, at the subsequent step S3, the image processor 35 maps a pixel value=0 in the area. This mapping generates the frame data $D_{FRAME}$ that retains the size of the rectangular detection surface Pall corresponding to the rectangular area having the zigzag pattern ZG.

Then, at step S4, the image processor 35 stores the frame data $D_{FRAME}$ in the first storage 34. The reception of the frame data, mapping of pixel value=0 and storage of the data are repeatedly performed at a give frame rate (step S5). Accordingly, by the time the rotational movement of the paired X-ray tube 21 and the detector 22 is completed, a number of frame data $D_{FRAME}$ will have been stored in the storage 34 through the series of scan sequences, the frame data $D_{FRAME}$ having been collected at a number of collection timings that are determined by the given frame rate.

Then, at step S6, the image processor 35 retrieves each of the plurality of frame data $D_{FRAME}$ stored in the first storage 34 and applies a sub-pixel technique thereto to determine pixel values for the retrieved frame data $D_{FRAME}$ according to area ratio. As schematically shown in FIG. 9(B), this generates a new rectangular frame data $D_{FRAME-A}$ which is formed of pixels S1 (<S) that are arranged along the first orthogonal-coordinate system (X1, Y1), each sub-pixel being smaller than the collecting pixel, i.e. the detection element S. Specifically, the raw frame data $D_{FRAME}$ collected under the second orthogonal-coordinate system (X2, Y2) is converted to the first orthogonal coordinate system (X1, Y1) using the field of view F1 which is virtually set with respect to the detection surface Pall, and then the frame data $D_{FRAME-A}$ based on the sub-pixels is generated. The field of view F1 is set as a virtual memory space VM in a memory of the image processor 35 (see FIG. 2).

Referring now to FIG. 10, hereinafter is described the concept of the sub-pixel technique for determining a pixel value of a sub-pixel according to area ratio.

As schematically shown in FIG. 10(A), the raw frame data $D_{FRAME}$ collected under the second orthogonal-coordinate system (X2, Y2) is expressed by four pixels P1 to P4 slanted upward to the right. These pixels have pixel values P1=2, P2=6, P3=6 and P4=2. As shown, an area K composed of sub-pixels is virtually set such as in the first storage 34. The area K has a size corresponding to the field of view F1 (e.g., width 5.8 mm in the direction of the first X-axis X1) that is set in the virtual memory space VM with respect to the detection surface Pall. The area K, which is composed of sixteen sub-pixels K1 to K16 and is in a square shape, for example, is arranged along the first orthogonal-coordinate system (X1, Y1). The collecting pixel P1 (to P4) has an area that is ¼ of that of the sub-pixel K1 (to K16). The square area composed of the four pixels P1 to P4 of the frame data $D_{FRAME}$ is superimposed over the area K composed of the sixteen sub-pixels K1 to K16, with the oblique angle α=14.08° being retained and with the center positions being permitted to coincide.

As a result, as shown in FIG. 10(B), the obliquely arrayed large pixels P1 to P4 are superimposed over the small square areas of the sub-pixels K1 to K16 so as to obliquely divide the small square areas, with the center position being permitted to coincide. The "area ratio" referred to in the following description means the proportion of an area, in which the obliquely arranged pixel P1 (to P4) overlaps with the non-oblique sub-pixel K1 (to K16), occupying in the pixel P1 (to P4). The sub-pixels K1 to K16 have given point symmetric properties about area ratio with respect to the pixels P1 to P4 superimposed over them. Accordingly, as shown, the sub-pixels K1 to K16 can each be treated as a set composed of four sub-pixels A, B, C and D. Taking account the point symmetric properties, the sub-pixels A to D are arranged as shown in FIG. 10(A). In this case, the following expression is established:

"Area ratio of sub-pixel A+area ratio of sub-pixel B+area ratio of sub-pixel C+area ratio of sub-pixel D=1=area ratio of each pixel P1 (to P4)"

For example, when partial areas in which the sub-pixels A to D overlap with the pixels P1 to P4 are indicated by a, b, c1, d1, c2 and d2 in FIG. 10(A), the area ratios of the partial areas a, b, c1, d1, c2 and d2, for example, are:

a=0.16, b=0.25, c1=0.13, d1=0.22, c2=0.09 and d2=0.03

Accordingly, the pixel values of the sub-pixels A, B, C and D along the first orthogonal-coordinate system (X1, Y1) will be as follows, using the pixel values of the obliquely arranged pixels P1 to P4 (along the second orthogonal-coordinate system (X2, Y2)) on the basis of the sub-pixel technique taking account of area ratio:

Pixel value of sub-pixel A=(2×a)×gain
Pixel value of sub-pixel B=(2×b)×gain
Pixel value of sub-pixel C=(2×c1+6×c2)×gain
Pixel value of sub-pixel D=(2×d1+6×d2)×gain Here, the numeral 2 is a pixel value of the pixel P1, the numeral 6 is a pixel value of the pixel P3, and gain is a coefficient that is set to make clear the image made up of the sub-pixels, the coefficient being a constant value (e.g., gain=2).

For example, in terms of the sub-pixel K1 (=A), K2 (=B), K5 (=C) and K6 (=D), the following are obtained:

Pixel value of sub-pixel K1 (=A)=2×0.16×2=0.64
Pixel value of sub-pixel K2 (=B)=2×0.25×2=1
Pixel value of sub-pixel K5 (=C)=(2×0.13+6×0.09)×2=1.6
Pixel value of sub-pixel K6 (=D)=(2×0.22+6×0.03)×2=1.24

Since other sub-pixels K3, K4, K7, K8, K19 to K16 correspond to the collection of three groups each being composed of the sub-pixels A to D, the pixel values thereof can be similarly calculated.

The sub-pixels K1 to K12 are calculated from the pixel values of the pixels P1 to P4, which depends on the area ratio with which the collecting pixels P1 to P4 occupy each of the sub-pixels K1 to K12. In the example shown in FIG. 10(A), the sub-pixels K1 to K12 as shown in FIG. 10(B) are obtained. Although the number of the pixels of the actually collected frame data $D_{FRAME}$ is much larger, in principle, the sub-pixel technique based on area ratio is carried out using the calculation described above.

As a result of applying the sub-pixel technique, the frame data $D_{FRAME-A}$ (see FIG. 9(B)) equivalent to the number of collections are stored in the storage 34, the frame data $D_{FRAME-A}$ having been mapped along the first orthogonal-coordinate system (X1, Y1) that coincides with the scan direction. At step S7, the image processor 35 performs image processing with respect to each of the frame data $D_{FRAME-A}$ to improve image uniformity. The image uniformity refers to the degree of uniformity in the detection characteristics of the detector when radiation (X-rays and gamma rays) assumed to be uniform is applied to the detector 22. The reasons why such image processing is necessary are described below.

In general, as described above, when the plurality of modules M are placed side by side on a single plane as in the detector 22 of the present embodiment, the gap G (e.g., see FIGS. 4 and 6) is required to be provided between the plurality of modules M. When the gap G is required to be provided, the width of the gap G is required to be accurately controlled and to perform image processing raising awareness about the absence of the collecting pixels in the area of the gap G. In the present embodiment, the pixel value=0 is applied to the collecting pixels that correspond to the area of the gap G to perform image processing accordingly (step S3). Nevertheless, non-uniformity (a band of periodical artifacts or the like) may appear in the reconstructed image due to the influence of the gap G, i.e. the absence of the collecting pixels.

Figure 11:
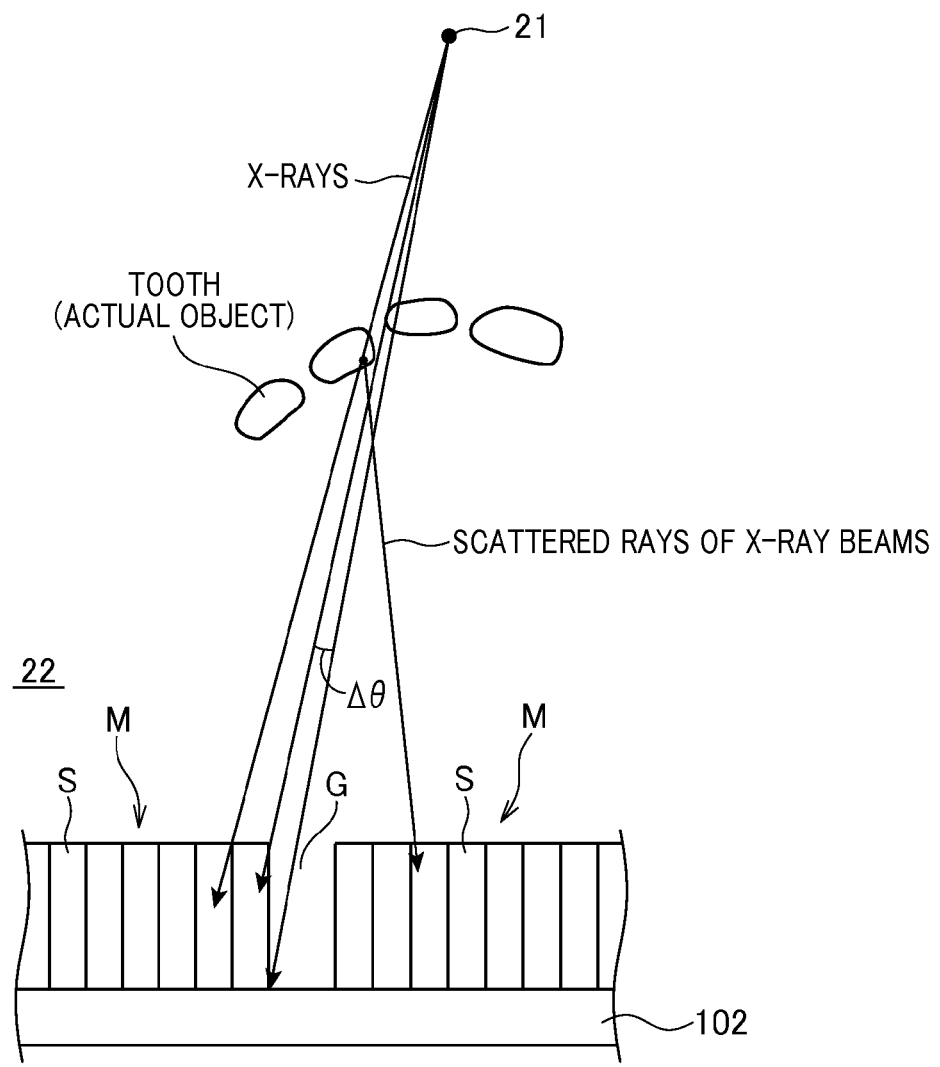
FIG. 11 is a diagram explaining drawbacks caused by gaps formed among the modules.

The inventors of the present invention have analyzed the occurrence factors of the non-uniformity. In general, when there is the gap G in between the modules M of an X-ray detector, the solid angle of an incoming X-ray in a single view depends on the position of each of the pixels (detection elements S) configuring the modules M. Further, the solid angle of an incoming X-ray considerably differs between pixels that form an end portion of a module M and the pixels positioned on an inner side of the module M than the end-forming modules. Specifically, as shown in FIG. 11, in the end-forming pixels of a module M, an X-ray is incident on the module M with a solid angle larger by $\Delta\theta$ than on the inner pixels. Accordingly, in one module M, the detection sensitivity differs between the pixels. The presence of the area of the gap G more emphasizes the difference in the detection sensitivity and a band of distortion is likely to be caused in an image. In order to remove the distortion, the image may be scanned and reconstructed, followed by post-processing to correct the non-uniformity caused by the gaps. However, the post-processing can still leave distortion in the image and the image may be unsuitable for use.

Various reasons as follows may be enumerated as the causes of the incomplete removal of non-uniformity even performing the post-processing. One of the reasons is associated with the detection sensitivity. Specifically, as shown in FIG. 11, the solid angle of an incoming X-ray depends on the pixels (elements S), i.e. depends on positions including the position of the gap G. Also, scattered X-rays will be caused in a substantive object (i.e. imaged site of the object being examined), such as teeth and chin portion. Therefore, the detection sensitivity may be complicatedly varied even in the area of the gap G. Another reason may be originated from the preconditions of image reconstruction. When a panoramic image is reconstructed, a shift-and-add process is performed. If a substantive object is present in the plane to be reconstructed, the portion is precisely visualized (visualized correctly reflecting the size of the portion) in the reconstructed image. However, in the otherwise situation, it is not known how the object being examined will be visualized in the reconstructed image and no correct visualization is guaranteed. This may also be one of the reasons. Specifically, the pixel values of the peripheral portions of a module M in the reconstructed panoramic image have been processed on the premise that the object being examined is present in the plane to be reconstructed. When there is an obstructive shadow in the panoramic imaging or when the oral portion is offset from the panoramic trajectory, the object being examined (substantive object) would not be present in the plane to be reconstructed. Therefore, it is not a correct processing to estimate the values of the pixels positioned in the gap from the pixels in the periphery of the module, on the basis of the reconstructed image. Accordingly, no accurate estimated values will be obtained.

In this regard, the inventors of the present invention have paid attention to the matter that the data that possess information, as it is without breaking it, of the position and the form of the substantive object correspond to the frame data that have been collected from the detector 22 or the data resulting from mapping the frame data in a virtual memory space as will be described later. In other words, in order to enhance uniformity of a reconstructed image, it is essentially important to preprocess data before being subjected to the shift-and-add process in image reconstruction.

Taking account of this, in the present embodiment, the image processor 35 applies, at step S7, the following two image processes as preprocesses, independently or in combination, to the plurality of frame data $D_{FRAME-A}$, i.e. the image data before being reconstructed, on a frame basis.

(1) Areas having no data of the gap G are estimated from the pixel values in the vicinity of both end portions of each module M for complementation; or (2) When the movement of the detector 22 can be correctly estimated or detected, the oblique mounting of the detector 22 is advantageously used to calculate the data corresponding to the area of the gap 22 from the pixels around this area in the frame data, the pixels carrying true data, and the pixels of the area of the gap G are embedded with the pixel values.

Alternative to the estimation and complementation processing of the above item (1), the processing may be performed at the stage of completing mapping of the collected plurality of frame data $D_{FRAME}$ in the virtual memory space. In other words, this processing is performed as preprocessing at step S6, which will be described later, in applying the sub-pixel technique based on area ratio.

Specifically, these improvement processings for image uniformity may preferably be performed prior to image reconstruction described later. Once image reconstruction is performed, it is not easy to uniform an image for the reasons set forth above. In contrast, in the present embodiment, the processes for improving image uniformity of the above item (1) and/or (2) are performed prior to image reconstruction. Accordingly, distortion of an image due to the presence of the gap G is more effectively estimated and reduced. As a matter of course, as a measure against the influence on the image uniformity due to the gaps that may still remain in some degree after use of the present processes, well-known correction technique may be applied as post-processing to the reconstructed image. Thus, image uniformity is complementarily enhanced.

At step S8, the image processor 35 applies an image reconstruction technique called shift-and-add technique to the plurality of frame data $D_{FRAME-A}$ after being applied with the processes of uniformity to reconstruct an image of a cross section along the tooth row, for example, of the object being examined P.

The sub-pixel technique for distributing pixel values according to area ratio and the shift-and-add process for image reconstruction described above may be performed as a single process.

The reconstructed image may suffer from an image unevenness which is attributed to statistical noise that may be caused in the lateral direction, i.e. in the direction of the first X-axis X1. In order to reduce such image unevenness, the image processor 35 carries out known post-processing (step S8), such as denoising or uniformity correction, and displays the processed image on the display unit 36 (step S9).

As described above, according to the panoramic imaging apparatus of the present embodiment, various advantageous effects as follows are obtained.

First of all, in the panoramic imaging apparatus related to the present embodiment, it is no longer necessary to detect an area that cannot contribute to image reconstruction, the area being generated in both end portions with reference to the scan direction. An X-ray radiation exposure amount is reduced accordingly. This may be simply explained referring to FIG. 12(A). Here, an obliquely arranged detector DEC based on conventional art is moved in a scan direction to perform the "conventional scan with oblique arrangement". In this case, when a required imaging area RGN is attempted to be ensured, extra scan has to be performed with respect to triangular portions RX on both ends of the area RGN with reference to the scan direction. In other words, X-ray radiation exposure is increased by an amount corresponding to the X-ray radiation with respect to these two portions RX.

As shown in FIG. 12 (B), according to the present embodiment, the pixels of the detector 22 are arranged being slanted by the angle $\alpha$, as described above, with reference to the scan direction, while the plurality of modules M are arranged in the longitudinal direction. Using this detector 22, scan (hereinafter referred to as oblique cascaded arrangement scan) is performed in the scan direction. In the "oblique cascaded arrangement scan", since the detector 22 is perpendicular to the scan direction (first X-axis X1), the scan of the detector 22 does not involve the extra radiation exposure areas RX mentioned above. For this reason, the panoramic imaging apparatus of the present embodiment can significantly reduce the X-ray radiation exposure amount compared to the apparatus that uses an obliquely arranged detector based on conventional art.

The plurality of pixels, i.e. the plurality of detection segments S, of the detector 22 each have a comparatively small crossing angle, e.g. α=14.08°, with respect to the scan direction, and are moved in the scan direction in the obliquely arrayed posture. Accordingly, the position of each detection segment S that passes through a portion of the object being examined P varies, with regard to a position in the direction of the second Y-axis Y2, with the progress of the scan. This allows the pixels of the frame data $D_{FRAME}$ detected at the collection timings to also include variation components of the pixel values in relation to not only the lateral direction (first X-axis X1) but also the longitudinal direction (first Y-axis Y1) at the same point. Thus, in a reconstructed image of the present embodiment, the distortion unique to a digital image is reduced and resolution is improved in both of the longitudinal and lateral directions of the reconstructed image, compared to the reconstructed image produced by an imaging apparatus that uses a detector based on conventional art in which the array of pixels is not obliquely provided with respect to the scan direction.

Referring to FIGS. 13 to 17, improvement of resolution is schematically described in detail. This description is based on the simulations actually performed by the inventors of the present invention.

As shown in FIG. 13(A), a crisscross structure (indicated by oblique lines) PX is assumed to be present in the object being examined P. The X-ray that has passed through the structure PX produces a pixel value=1 for each virtual cell Rima and produces a pixel value=0 for the rest of the portions. The virtual cell Rima is virtually provided to schematically count pixel values. The X-ray that has passed through the object being examined P is detected by the detector 22. In this case, the number of the detection pixels (detection elements S) of the detector 22 is schematically four, i.e. P1 to P4. The second orthogonal-coordinate system (X2, Y2) of the detection pixels of the detector 22 is permitted to coincide with the first orthogonal-coordinate system (X1, Y1) along the scan direction to perform the conventional scan without the oblique arrangement of the modules that is not the scan based on the oblique cascaded arrangement described above. The scanning pitch is ½ pixel. In other words, the X-ray tube 21 and the detector 22 in a pair move at the pitch of ½ pixel with respect to the object being examined P. With this movement, a detection area Rdec moves pitch by pitch, as shown, along the scan direction. One image is shot at every movement of the pair to thereby generate, as shown in FIG. 13(B), seven frame data $D_{FRAME-1}$ to $D_{FRAME-7}$ of Seqs. 1 to 7. The detection pixels of the seven frame data $D_{FRAME-1}$ to $D_{FRAME-7}$ include pixel values that correspond to the number of the virtual cells Rima present on the structure PX, which are detected at the individual shots. For example, the detection pixel P1 of the frame data $D_{FRAME-1}$ of Seq. 1 includes two virtual cells Rima on the structure PX and hence has a pixel value=2. The detection pixel P2 of the frame data $D_{FRAME-3}$ of Seq. 3 includes ten virtual cells Rima on the structure PX and hence has a pixel value=10. This resultantly corresponds to the application of the sub-pixel technique that is a kind of shift-and-add process in which the seven frame data $D_{FRAME-1}$ to $D_{FRAME-7}$ are moved on the basis of the movement=½ pixel, while mutually adding the pixel values. Thus, as shown in FIG. 13(C), a reconstructed image Pimage-A of sub-pixels Psub is generated, in which the pixel values are distributed according to area ratio. Here, the size of each sub-pixel Psub is ½ of each detection pixel P1 (to P4).

Figure 13:
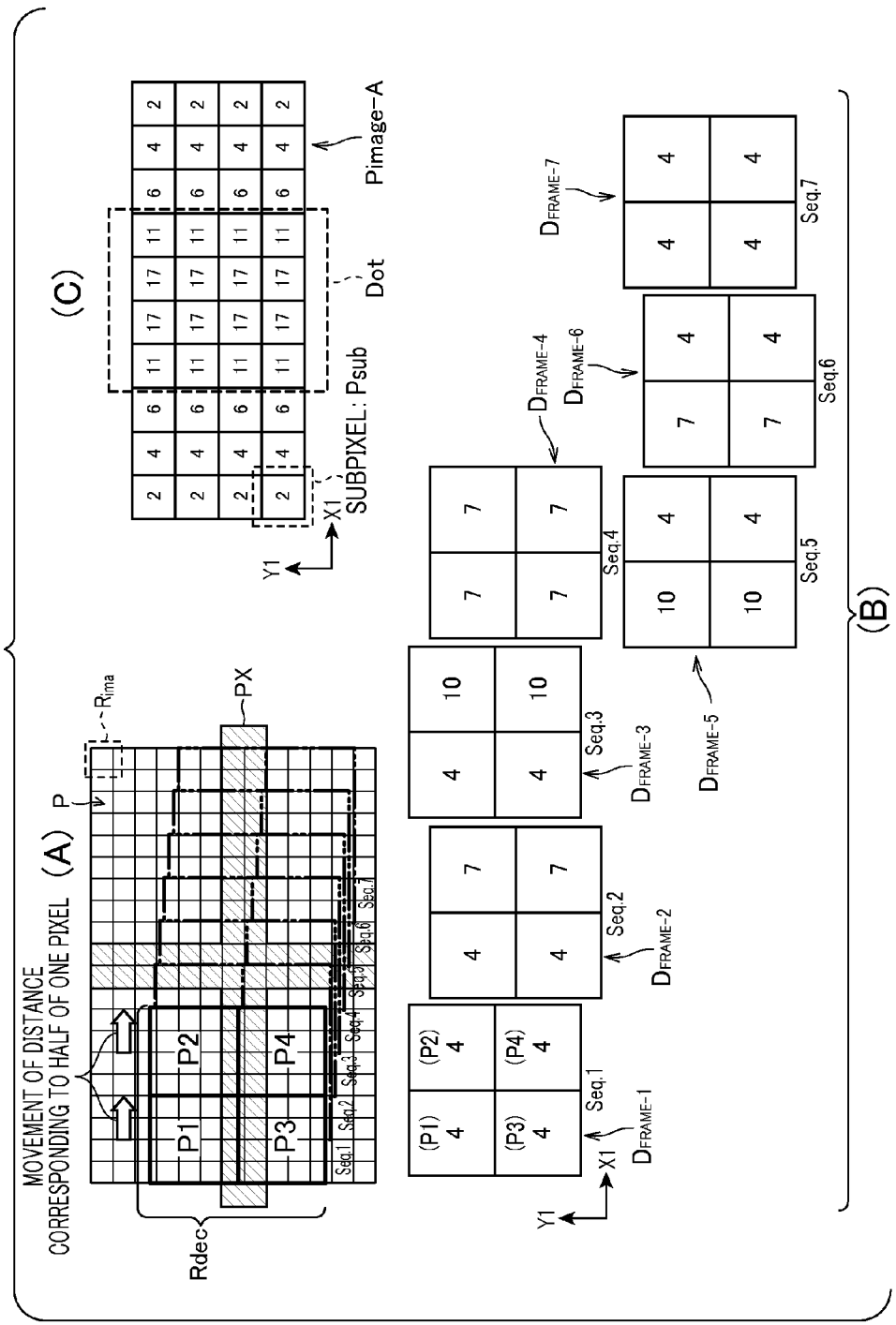
FIG. 13 provides diagrams explaining a process for a conventional sub-pixel technique.
Figure 14:
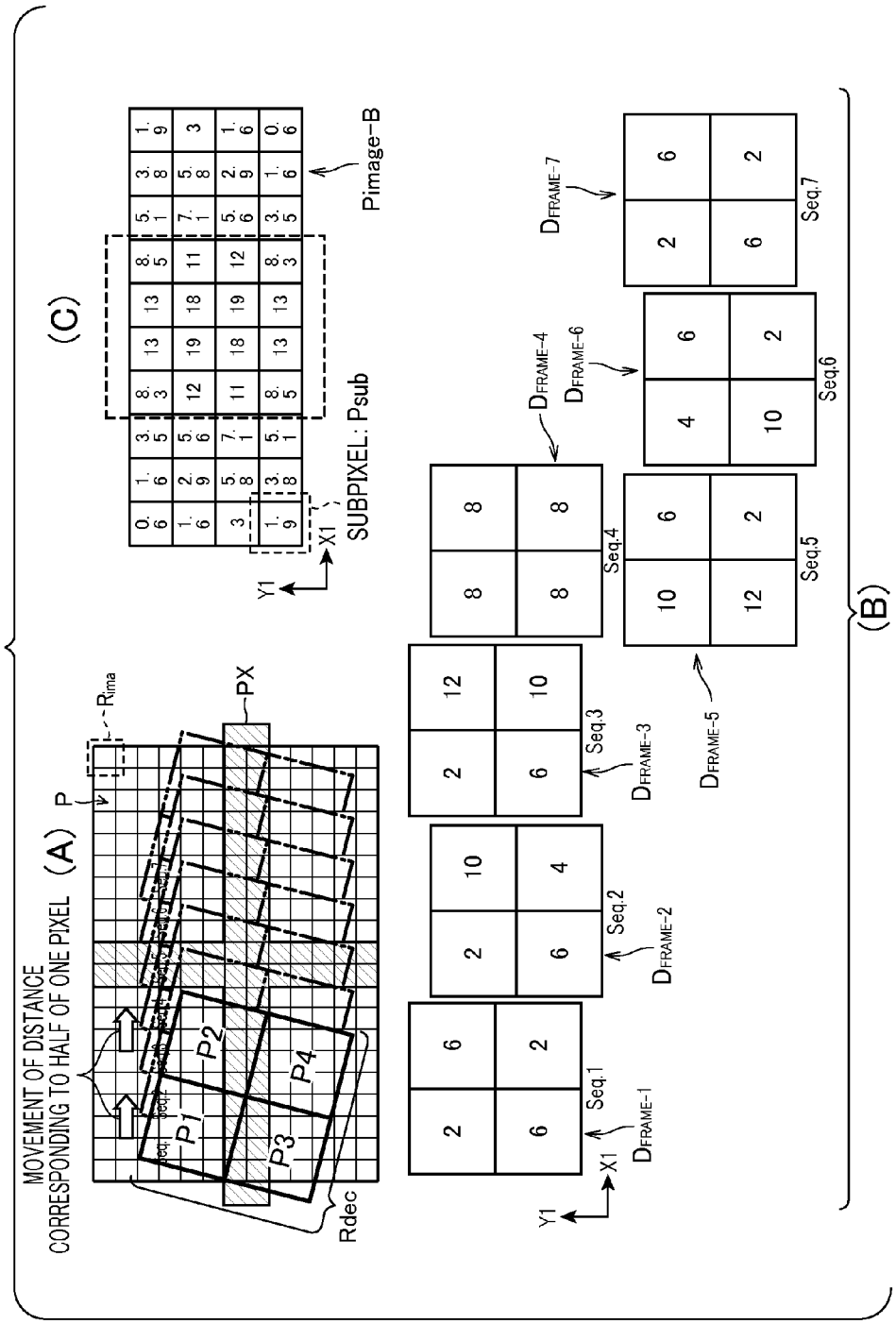
FIG. 14 provides diagrams explaining a process for the sub-pixel technique based on area ratios, which is according to the present invention.

FIG. 14 shows a scan with the oblique cascaded arrangement, according to the present invention, which is performed under the same conditions as those of the conventional scan shown in FIG. 13. FIG. 14(A) shows seven Seqs. 1 to 7 in the scan direction, relative to shooting positions. FIG. 14(B) shows seven frame data $D_{FRAME-1}$ to $D_{FRAME-7}$ and their pixel values in the respective Seqs. 1 to 7. FIG. 14(C) shows, similar to the above, a reconstructed image Pimage-B of sub-pixels Psub, in which the pixel values are distributed according to area ratio. In applying the sub-pixel technique, the area ratio and the pixel values of the sub-pixels Psub are calculated under the same conditions as those described referring to FIG. 10. As a result, as will be understood from FIG. 14(C), the reconstructed image Pimage-B includes sub-pixels Psub having pixel values that emphasize the site where the structure PX of the object being examined P is present, in both of the lateral and longitudinal directions (i.e. both of the directions in the first X-axis X1 and the first Y-axis Y1), compared to the sub-pixels of the normal scan (see FIG. 14(C)). Specifically, a larger pixel value is obtained in a denser portion of the structure PX, such as in the crossing portion. This is distinguishable from the result of the conventional scan with no oblique arrangement, in which unchanged pixel values are provided along the first Y-axis Y1. Such a conventional scan generates a featureless image, while the scan with the oblique cascaded arrangement generates a sharp image both in lateral and longitudinal directions. This will be clearly understood at a glance at the pixel values.

Figure 15:
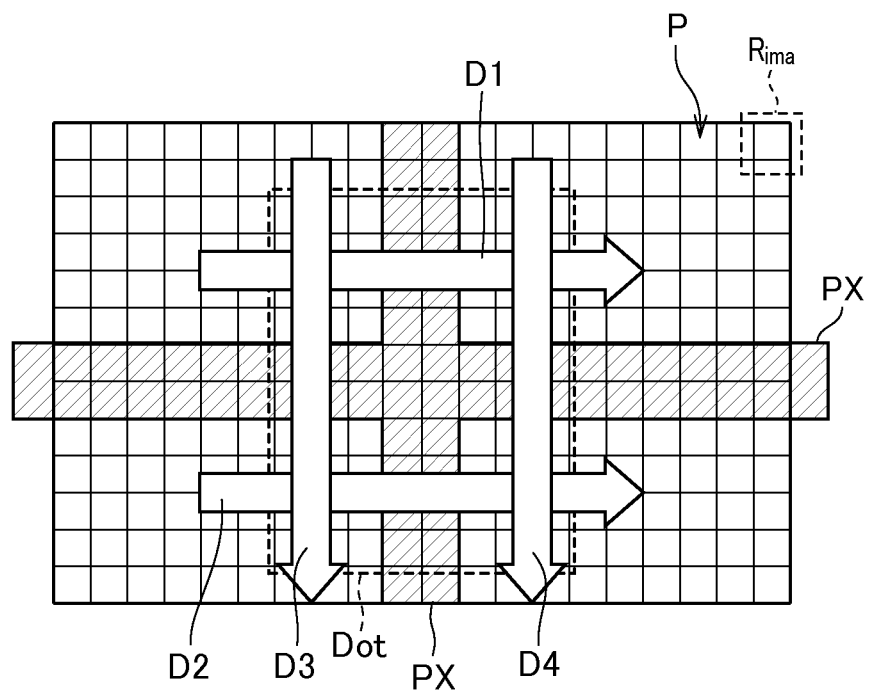
FIG. 15 is a diagram explaining plural directions along which profiles of pixel values are analyzed, which analysis is for comparison between a scan based on the oblique cascaded arrangement of modules in the present invention and a scan based on a conventional oblique arrangement of modules.

Let us study here the profiles of the pixel values resulting from the conventional scan with no oblique arrangement and from the scan with the oblique cascaded arrangement performed as described above. The differences are obvious. As shown in FIG. 15, with reference to an area Dot enclosed by the dotted line in the reconstructed images Pimage-A and Pimage-B, the positions of calculating the profiles reside in four directions D1, D2, D3 and D4, which are set in the horizontal direction at the top and bottom ends and in the vertical direction at the left and right ends. FIGS. 16(A) to 16(D) show the profiles of the pixel values calculated at positions in the four directions D1 to D4 in each of the reconstructed images Pimage-A and Pimage-B. FIG. 16(A) shows profiles along the direction D1 that is the horizontal direction at the top end of the center area Dot of each of the reconstructed images Pimage-A and Pimage-B. The horizontal axis indicates position along the direction D1 and the vertical axis indicates pixel value (relative value). The term "oblique/cascade" indicates a profile curve resulting from the scan with the oblique cascaded arrangement related to the present invention. The term "conventional" indicates a profile curve resulting from the conventional scan with no oblique arrangement. Similarly, FIG. 16(B) shows profiles along the direction D2 that is the horizontal direction at the top end of the center area Dot. FIG. 16(C) shows profiles along the direction D3 that is the vertical direction at the left end of the center area Dot. FIG. 16(D) shows profiles along the direction D4 that is the vertical direction at the right end of the center area Dot.

It will be understood from these profiles that the distortion due to digitization is effectively reduced even in the case of the digitization in which distortion is most likely to be caused, as in the present example, and that resolution is effectively recovered in reconstruction.

As described above, the reason why the resolution in both of the longitudinal and lateral directions are enhanced in the reconstructed image lies in that the groups of detection pixels are moved in the scan direction while each of the detection pixels is slanted with respect to the scan direction. Owing to this slant, the positional relationship between the object being examined and the detection pixels gradually changes in the detection area with the movement thereof, with respect to not only the scan direction but also the longitudinal direction. Thus, the same one point of the object being examined is captured by a plurality of different detection pixels to thereby allow the detection information of the detection pixels to include pixel-value-variation information in the longitudinal direction. Since this information is reflected in the reconstructed image, resolution is recovered in the longitudinal direction, as well, that is the direction along the first Y-axis Y1.

Figure 17:
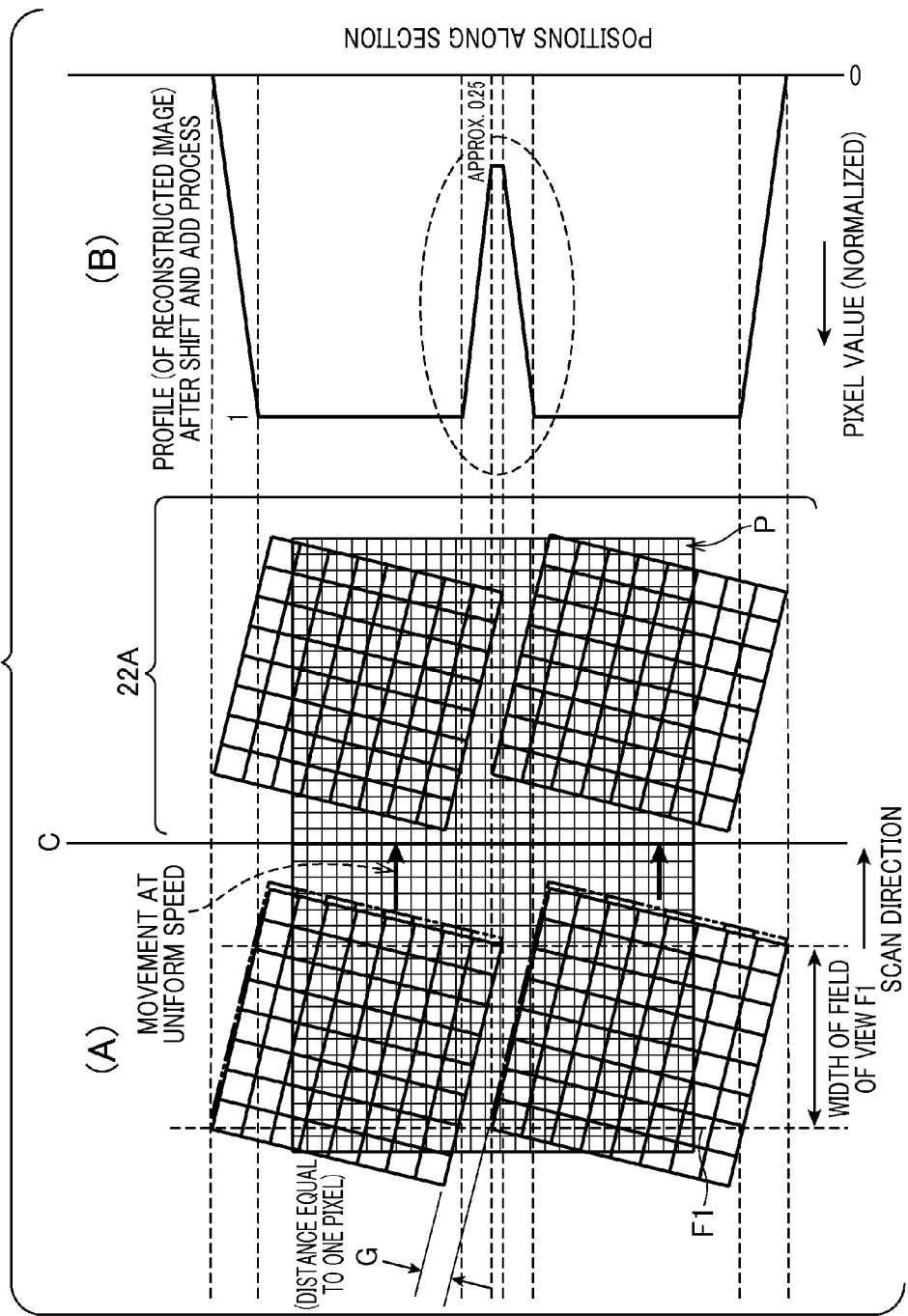
FIG. 17 is a diagram explaining another analysis of a pixel-value profile analysis in the embodiment.

How the resolution is recovered is shown in FIG. 17. FIG. 17(A) shows a simulation performed assuming the following conditions. The conditions are: that a detector 22A including two cascaded modules M each having a detection surface corresponding to 8×8 number of pixels is arranged in the oblique/cascade manner (slant $\alpha$=14.08° on the basis of the principle of the present invention; and that the detector 22A is moved in the scan direction at a constant speed with respect to the object being examined P, while an image is shot at a regular interval. A gap G corresponding to one pixel is provided between two modules M. A matrix provided as the object being examined P indicates sub-pixels as well in a virtual memory, each having a size that is ½ of each detection pixel of the detector 22A. The matrix is provided along the first orthogonal-coordinate system (X1, Y1). The effective field of view F1 used for coordinate conversion is set in a rectangle that internally contacts the detection surface of the detector 22A.

During the movement, a plurality of collection sequences are performed at a regular interval to collect a plurality of frame data. The frame data are applied, as described above, with the sub-pixel technique and the shift-and-add process according to area ratio to reconstruct an image of a cross section of the object being examined P.

FIG. 17(B) shows a profile of the pixel values in a plane in the reconstructed image, which is taken at a center position C of the matrix that indicates the object being examined P. In the profile, the horizontal axis indicates cross-sectional position and the vertical axis indicates pixel value (total number of sub-pixels on which the detection pixels are overlapped (i.e. collected)). As will be understood from this profile, the pixel values are smaller (pixel value=about 0.25) in the vicinity of the center position of the cross section, i.e. in the portion in which the gap G between the two modules M moves in the scan direction, than in other portions (specified as pixel value=1).

However, conversely, for the gap G, although collecting detection pixels are absent, a part of other detection pixels would alternatively collect the portion corresponding to the gap G in the object being examined to obtain a constant pixel value=about 0.25 (after being specified) at the smallest. The degree of pixel value of this much (about 0.25 at the smallest) allows uniformity correction following image reconstruction to exert its efficiency. The simulation performed by the inventors of the present invention has revealed that the uniformity correction can recover the pixel value to about 0.72 and that the influence on an image of having to provide the gap G between the modules M is greatly mitigated. In other words, the influence attributed to the absence of detection pixels from between the modules M is minimized in image reconstruction.

As described above, in performing the shift-and-add process, the detection pixels juxtaposed in the longitudinal direction (direction in the second Y-axis Y2) of each of the modules M can also contribute to the image reconstruction of the portions corresponding to the gaps G. Thus, advantageously, the artifacts due to the non-uniformity of pixels are unlikely to appear in the lateral direction (direction in the first X-axis X1) and the distortion that is likely to be caused in a digital image will hardly occur.

Further, in the present embodiment, the modules M (second X-axis X2) are slanted by $\alpha$=14.08° with respect to the scan direction (first X-axis X1) to provide the various advantages mentioned above. However, the slant angle $\alpha$ is not necessarily limited to 14.08° but may be about 14° taking account of the errors or the like caused in the manufacture or mounting. The simulation performed by the inventors of the present invention has revealed that the above advantages can be enjoyed by selecting the slant angle from a range of $6° \leq \alpha \leq 20.7°$.

Figure 18:
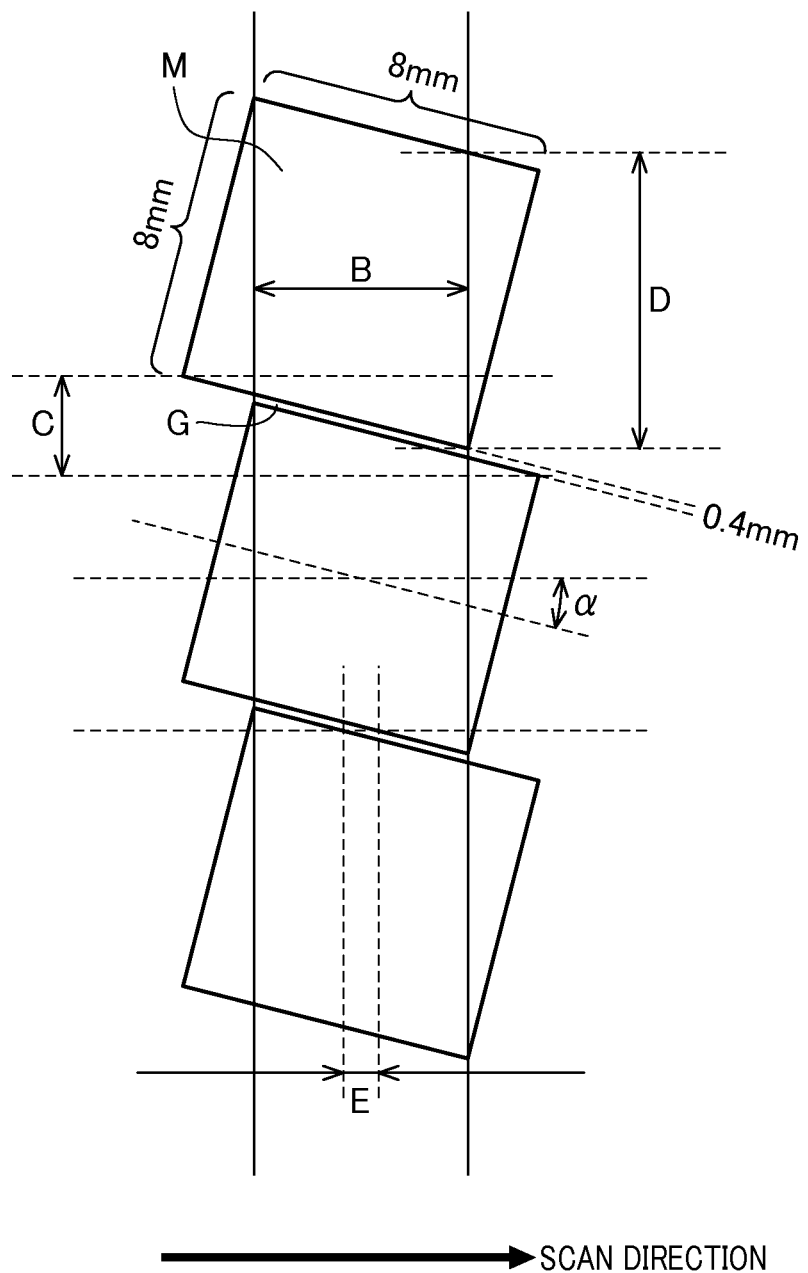
FIG. 18 is a diagram used for explaining an estimation of upper and lower limits of a gap formed between mutually adjacent modules.

Referring to FIG. 18, the angle range $6° \leq \alpha \leq 20.7°$ is explained. As shown in the figure, three square modules M each having a size of 8 mm×8 mm are obliquely arranged with respect to the scan direction. In the figure:

$\alpha$: angle between the scan direction that is the first X-axis X1 and each module M;

B: width of a field of view (corresponding to the field of view F1 described above) which is parallel to the axis (first Y-axis Y1) perpendicular to the scan direction and is in internal contact with the modules M; and C: distance that causes non-uniformity in the detection due to the influence of the gaps G (dead spaces) in the axial direction perpendicular to the scan direction.

Each gap G has a width of 0.4 mm.

In this geometry, as the angle $\alpha$ is made larger, the internally contacted field of view B (=F1) will have a smaller width in the scan direction, and the distance C will become larger. Specifically, these three physical quantities a, B and C are in a mutually contradictory relationship. There should be an angle $\alpha$ that establishes an appropriate relationship between these physical quantities. Assuming that such an angle $\alpha$=14°, the field of view B then will have a width=about 5.83 mm and the distance C=about 2.82 mm. A distance D=8.24. Accordingly:

Rate of area use of the X-ray incidence area    I)
of the detector that influences manufacturing cost =
$(B \times D/(8 \times 8)) \times 100 = (5.83 \times 8.24/(8 \times 8)) \times 100 =$ about 75%

Rate of area requiring uniformity correction of detection    II)
performed by the detector in the orthogonal-coordinate system,
the rate influencing the image quality = $(C/D) \times 100 =$ about 34%

Rate of influence to data in the gap $G$ in the scan direction,    III)
i.e. an indiction of easiness of correction =
$(E/B) \times 100 = (1.65/5.83) \times 100 =$ about 28%

The use rate of area=50% or more, the required area rate=50% or less, and the influence rate=50% or less can be provided as indexes of indicating the appropriateness of the angle $\alpha$ setting.

In the case of the example shown in FIG. 18, the angle $\alpha$ that satisfies the index of the use rate of area is $\alpha$<22.5°, the angle α that satisfies the index of the required area rate is α<20.7°, and the angle α that satisfies the index of the influence rate is α>6°. Accordingly, the range of the angle α that satisfies all of these three indexes is "6°<α<20.7°". In the case of this example, the shape of the detector is square and its size is 8 mm×8 mm. However, as far as the size is square, substantially the same conditions as explained above are established.

When the shape of the detector is not square, i.e. when the shape is rectangle and its aspect ratio is not 1:1, the indexes mentioned above will tremendously vary. Therefore, an adequate design taking account of this point is required. Conversely, as far as the shape of the detector is square, the range of the angle A will be easily optimized and the preferable angle range will resultantly be "6°<α<20.7°".

Further, according to the present embodiment, prior to image reconstruction, i.e. prior to the shift-and-add process, a process of uniforming an image to be reconstructed is performed. This can minimize the variation in the detection sensitivity, the variation being attributed to the presence of the gap G between the modules M of the detector 22, and can remarkably improve the uniformity of the reconstructed image.

As described above, the panoramic imaging apparatus related to the present embodiment can reduce the dead zones by performing scan with the oblique cascaded arrangement. Further, the panoramic imaging apparatus can more reduce the X-ray radiation exposure and at the same time can provide a cross-sectional image along a tooth row with high resolution and high accuracy, while ensuring more analog and natural feeling.

Second Embodiment

Referring to FIGS. 19 to 22, hereinafter is described a second embodiment of the radiation detector related to the present invention. In the present embodiment, the components identical with or similar to those in the first embodiment are given the same reference numerals for the sake of omitting or simplifying the description.

Figure 19:
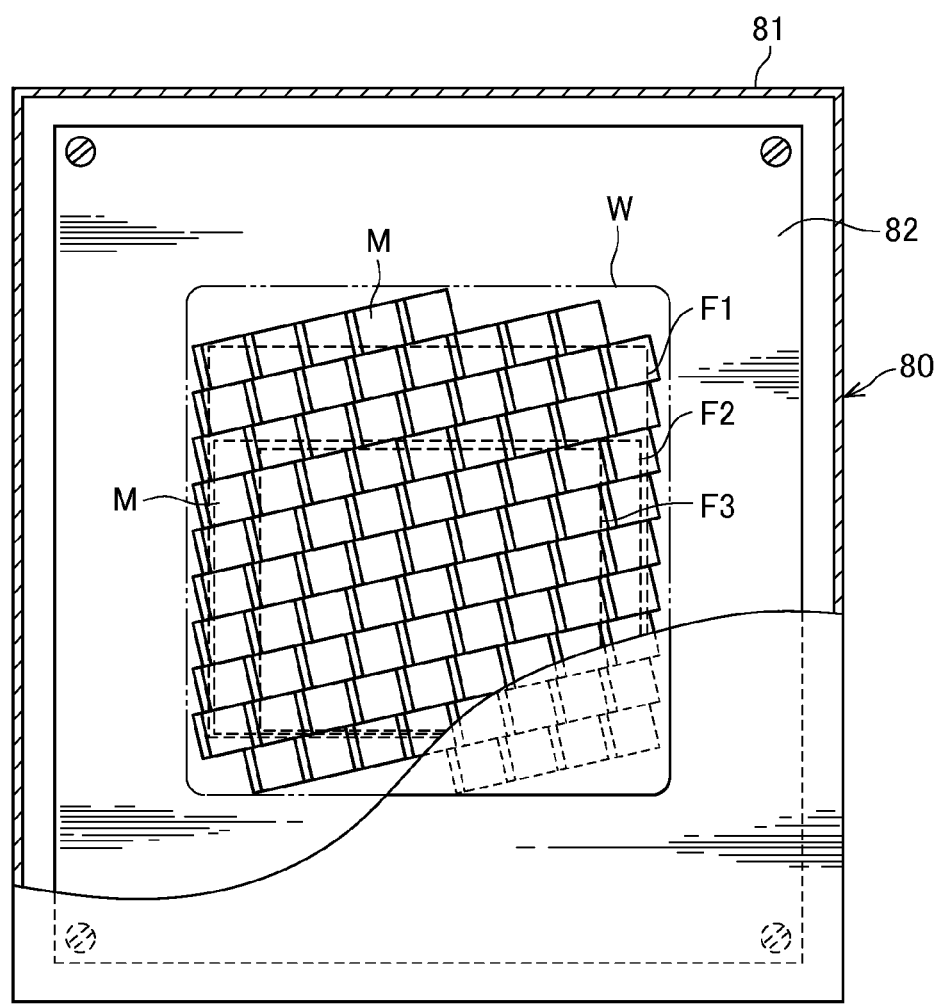
FIG. 19 is a plan view outlining a detector functioning as a radiation detector mounted in a CT scanner embodied as a radiation imaging apparatus according to a second embodiment of the present invention.

The present embodiment relates to an example in which the present invention is applied to an implemented X-ray CT (computed tomography) scanner. Since the configuration of the X-ray CT scanner is known, description is omitted. An X-ray detector 80 shown in FIG. 19 is applied to the X-ray CT scanner. Similar to the detector 22 described in the first embodiment, the detector 80 also includes a box-like housing 81 with a motherboard 82 being arranged inside. The housing 81 has an upper surface in which a rectangular X-ray incidence window W is formed. The motherboard 82 located right beneath the incidence window W has an upper surface in which a plurality of modules M are arrayed. The modules M are the same as those described in the first embodiment and each of the X-ray detection surfaces is in a square shape (8 mm×8 mm). Specific structure of each of the modules M is also the same as that described in the first embodiment.

Figure 20:
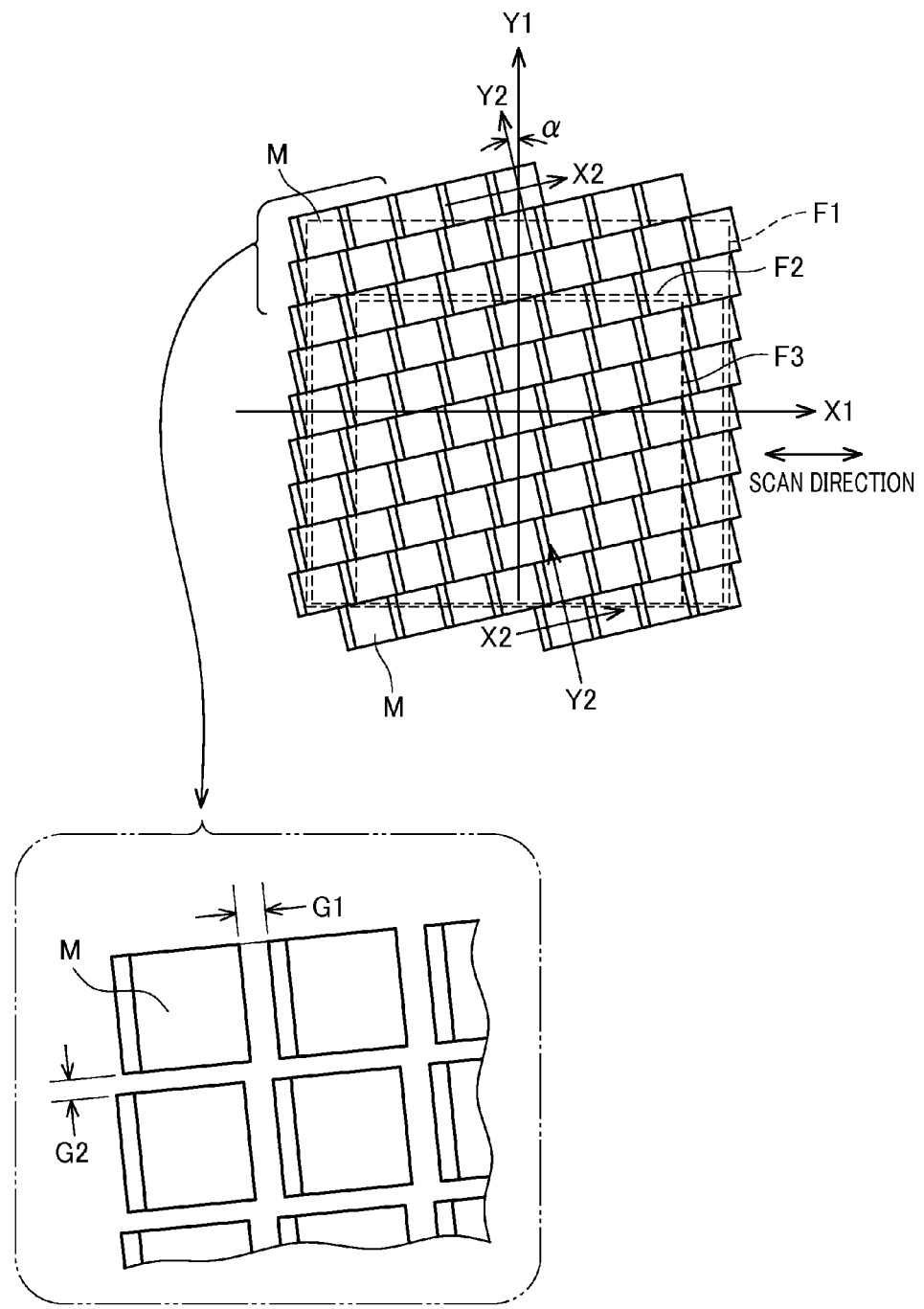
FIG. 20 is a structural diagram showing a two-dimensional arrangement of modules incorporated in the detector in the second embodiment.

As shown in FIG. 20, the plurality of modules M as a whole are two-dimensionally arrayed in a matrix-like manner along the first orthogonal-coordinate system composed of the first X-axis X1 and the first Y-axis Y1. On the other hand, a plurality of detection elements S configuring each of the modules M are also two-dimensionally arrayed, similar to the first embodiment, in a matrix-like manner along the second orthogonal-coordinate system composed of the second X-axis X2 and the second Y-axis Y2.

Each module M is arranged being slanted upward to the right (or slanted upward to the left) by the angle α with respect to the scan direction, i.e. the first X-axis X1. In other words, the plurality of modules M are mounted in an oblique cascaded arrangement. In both of the directions of the first X-axis X1 and the first Y-axis Y1, gaps G1 and G2, respectively, are provided between two adjacent modules M (see FIG. 18). These gaps, each having a known width, are necessary in adjacently arranging the plurality of modules on a single plane. The gaps G1 and G2 may only have to have a known width which, for example, may be an integral multiple of 1/N (N is an integer of two or more) of the size of each of pixels configured by the detection elements S. The gap G1 in the direction of the second X-axis X2 may be the same as or may be different from the gap G2 in the direction of the second Y-axis Y2. For example, the relationship may be G1>G2. A virtual field of view can be variably set in the detector 80. For example, an internally contacted field of view F1, or a field of view F2 or F3 completely residing inside may be used.

Figure 21:
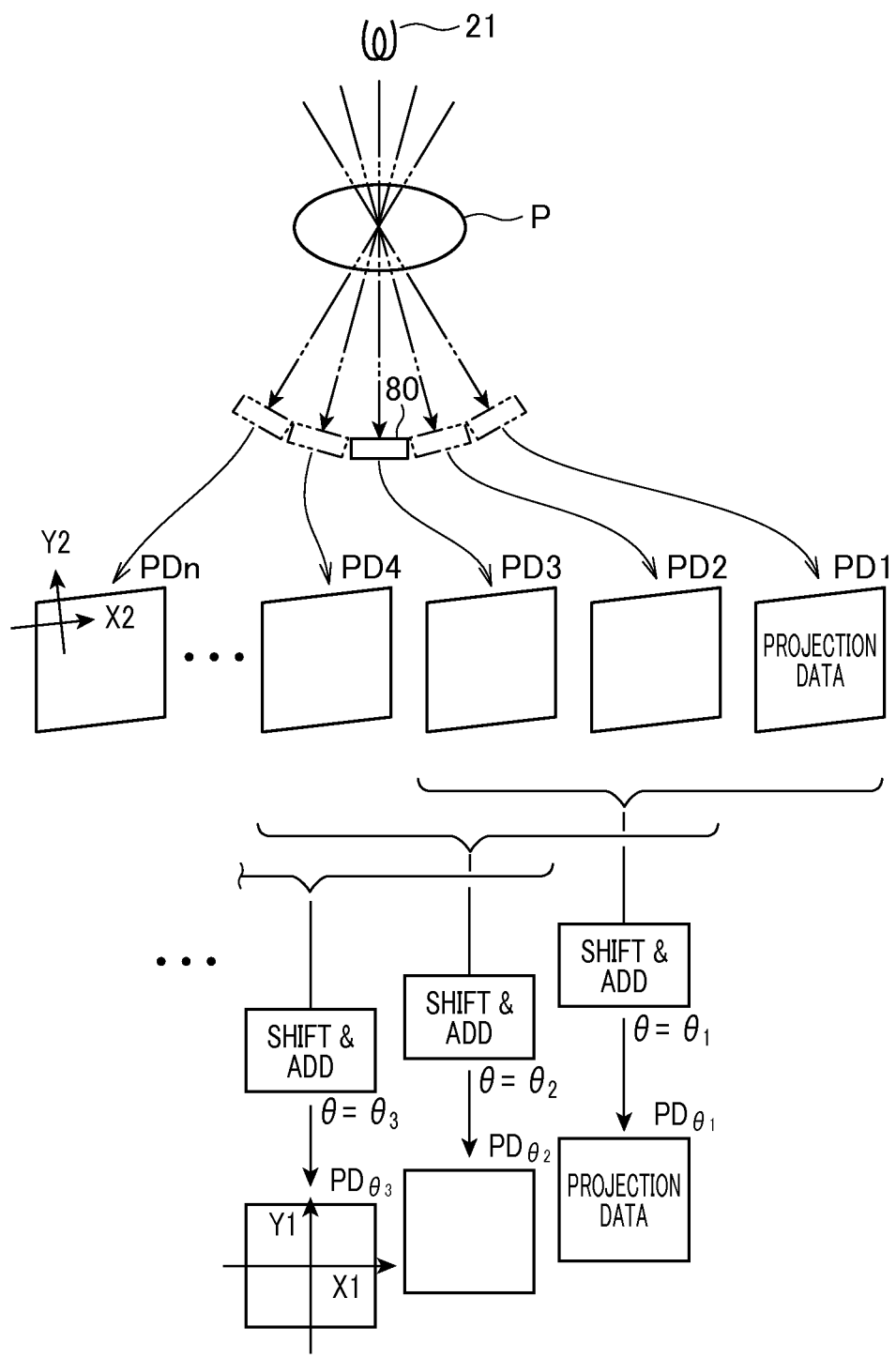
FIG. 21 is an illustration showing how to perform the sub-pixel technique based on area ratios, which is performed in the CT scanner according to the second embodiment.

As is well known and as shown in FIG. 21, when the object being examined P is scanned using the detector 80, the X-ray tube 21 and the detector 80 in a pair are rotated in the gantry (not shown). The object being examined P is located in a cylindrical dome of the gantry G. During the rotation, an X-ray is radiated from the X-ray tube 21 at a regular interval. Every time an X-ray transmits through the object being examined P, the X-ray is detected by the opposed detector 80. Specifically, for each projection angle during the rotation, digital projection data (frame data) is outputted from the detector 80. The projection data corresponds to detection data based on the oblique cascaded arrangement. The projection data collected through the detection are indicated by PD1, PD2, PD3, . . . PDn. For example, when the shift-and-add process described above is performed using the projection data PD1, PD2 and PD3 of a plurality of frames that are chronologically close to each other, projection data $PD_{\theta 1}$ is obtained, which has been converted to the first orthogonal-coordinate system (X1, Y1) at a projection angle θ=θ1. Similarly, when the shift-and-add process described above is performed using the projection data PD2, PD3 and PD4, projection data $PD_{\theta 2}$ is obtained, which has been converted to the first orthogonal-coordinate system (X1, Y1) at a projection angle θ=θ2. Repeating this, the original projection data PD1, PD2, PD3, . . . , PDn can be converted to projection data $PD_{\theta n}$ of the first orthogonal-coordinate system along the scan direction at a projection angle (timing) different from the projection angle of collecting the original projection data (collecting timing). In this way, the pixel values in the areas of the gaps G can be automatically complimented. By applying a well-known reconstruction technique to the projection data $PD_{\theta n}$, a CT tomographic image is obtained.

In the present embodiment, in order to achieve such a configuration, data of each view are collected at a speed faster than the frame collection speed required for the reconstruction in normal CT, and at a finer pitch. The detector 22 of the present embodiment is a semiconductor detector of direct conversion type, which is suitable for such a high-speed data collection.

Thus, the plurality of modules M are arranged along the scan direction, being oblique thereto, but arrayed in a direction perpendicular to the scan direction. Therefore, the detector 80 can enjoy the advantages of the detector according to the first embodiment described above, while providing a two-dimensionally widely expanded X-ray incidence surface. Accordingly, the X-ray CT scanner mounting the detector 80 also creates no dead zones and can much more reduce X-ray radiation exposure, while providing high-resolution X-ray tomographic image with more analog and natural feeling.

(Modifications)

Figure 22:
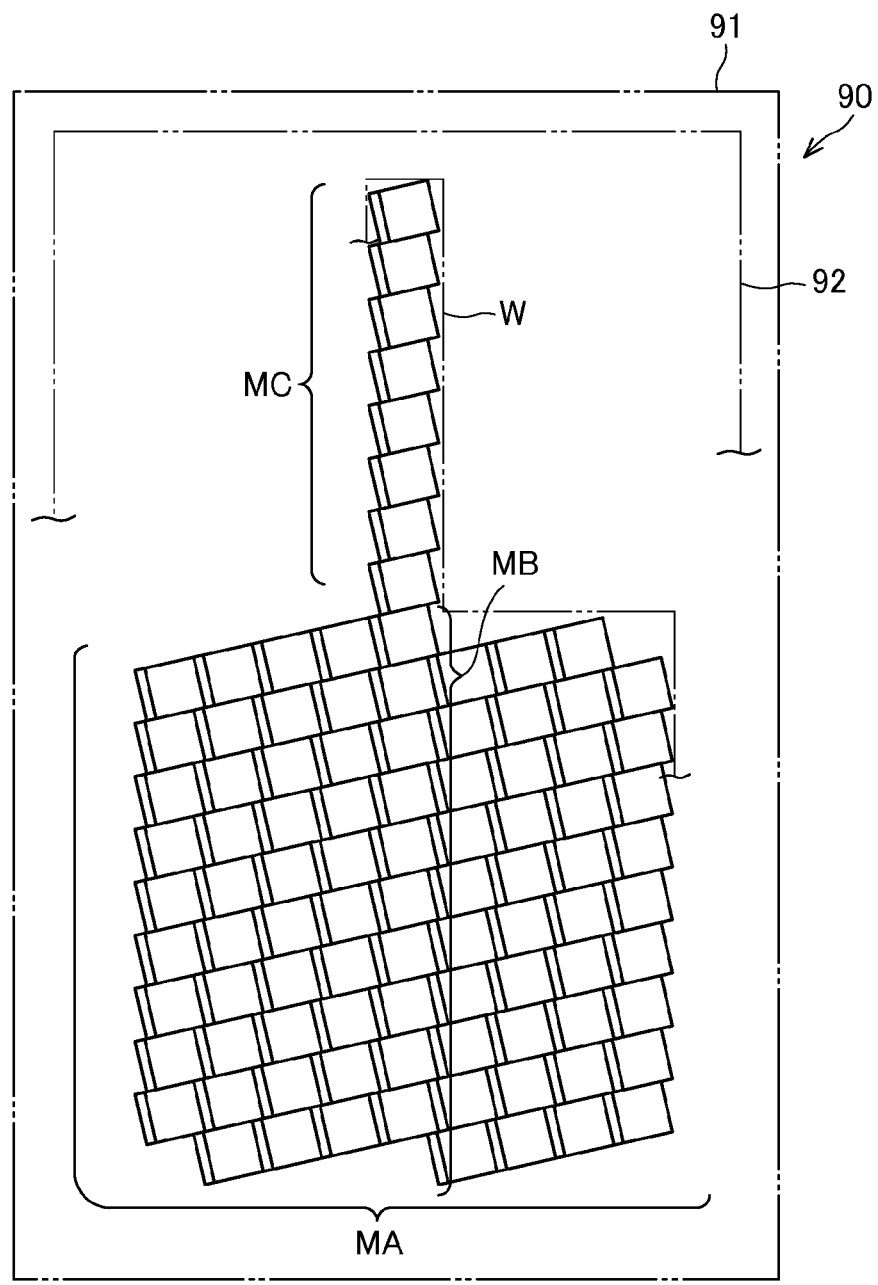
FIG. 22 is a plan view explaining arrangement of modules in a detector functioning as a radiation detector according to a modification.

FIG. 22 shows an X-ray detector 90 according to a first modification of the embodiments described above. As shown, the detector 90 also includes a motherboard 92 in a housing 91. On a single plane of the motherboard 92, an array of modules are provided, the array being a combination of the array of the modules M of the detector 22 described in the first embodiment and the array of the modules M of the detector 80 described in the second embodiment. The structure and arrangement of each of the modules M are the same as those of the above embodiments.

The characteristics of this oblique cascaded arrangement are as follows. A group MA of the plurality of modules M that are two-dimensionally arrayed along the first X-axis X1 (scan direction) and the first Y-axis Y1 additionally includes a module array MB at the center with reference to the direction of the first X-axis X1 (lateral direction), the module array MB alone being extended along the direction of the first Y-axis Y1 (longitudinal direction). In other words, a module group MC is projected in the longitudinal direction from the module group MA. The X-ray incidence window W is also formed in conformity with the module-arrayed structure of the "two dimension+one dimension (two dimension in terms of the pixels)".

This is because the detector 90 is permitted to serve both as a detector for panoramic imaging and a detector for X-ray CT. In panoramic imaging, the module groups MB and MC alone are used on a signal processing side. In X-ray CT, the module group MA alone is used on the signal processing side. Thus, one detector 90 can cope with both of the modalities, enhancing general purpose properties.

Figure 23:
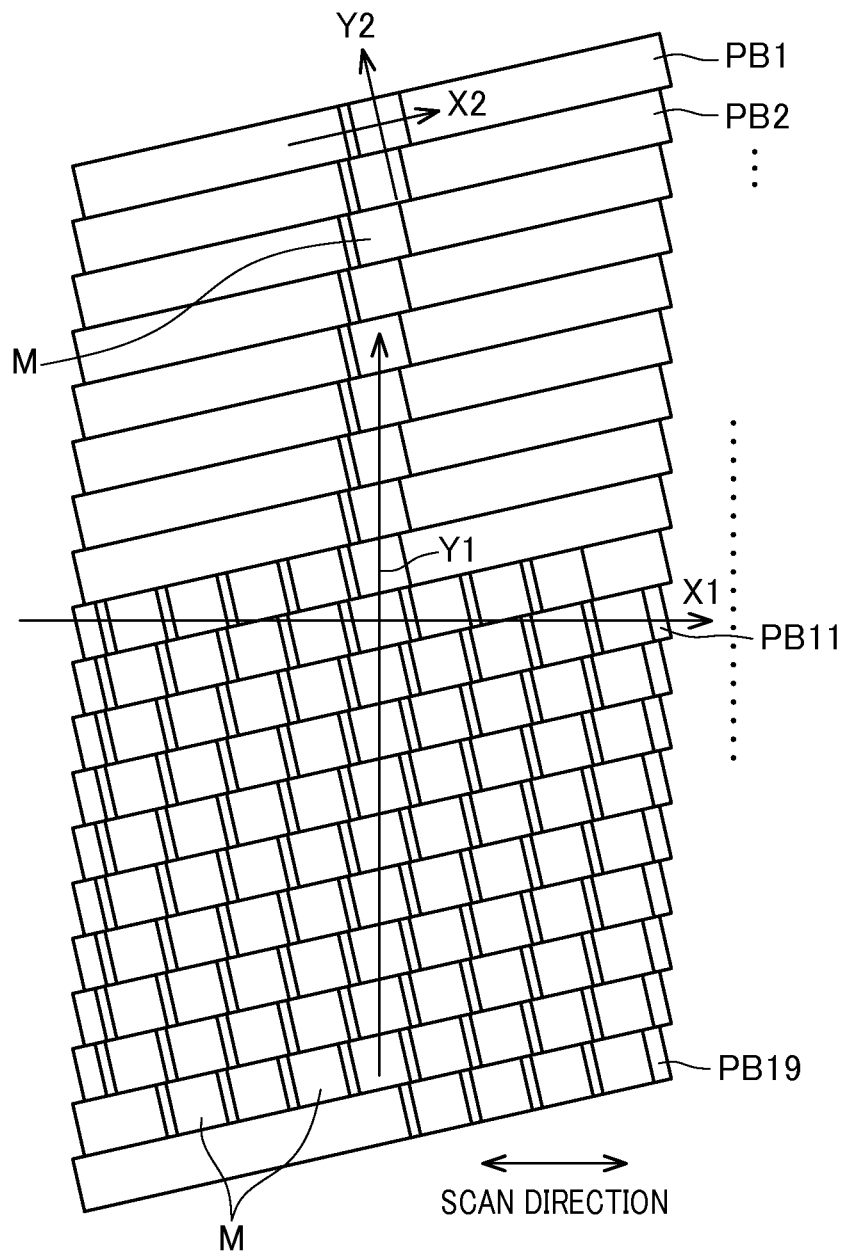
FIG. 23 is a structural diagram explaining how to produce a detector, especially, how to arrange modules, according to another modification.

FIG. 23 shows how the modules M are mounted in the detector 90 of dual purpose type shown in FIG. 22. As shown in FIG. 23, a plurality of module-mounted boards (printed boards) PB1 to PBn are prepared, which have the same size and the same length in the long side. The boards PB1 to PBn each have a width larger than the length of each module M in the direction of the second Y-axis Y2 by an amount corresponding to the gap G.

A desired number of modules M are mounted at desired positions of the module-mounted board PB1 (to PBn). As shown, the mounting is performed in accordance with the shape of the detection surface desired to be configured. Taking the first module-mounted board PB1 as an example, one module M is mounted at the center position with reference to the lateral direction. Taking the eleventh module-mounted board PB11 as an example, nine modules M are mounted at respective predetermined positions in the lateral direction.

Then, these module-mounted boards PB1 to PBn are obliquely arranged such as on a motherboard, not shown, at the angle α with respect to the first X-axis X1 determined to be the scan direction. In this case, the module-mounted boards may just be arranged being in contact with each other. Accordingly, although not shown, the gaps G are automatically set in the direction of the second Y-axis Y2. Both or either one of the ends of each module-mounted board PB1 (to PBn) are/is provided with a signal line which is connected to the motherboard.

Since the module-mounted boards have the same size and the same shape and the shape is rectangle, the modules can be easily mounted and the manufacturing cost of the detector is minimized.

Figure 24:
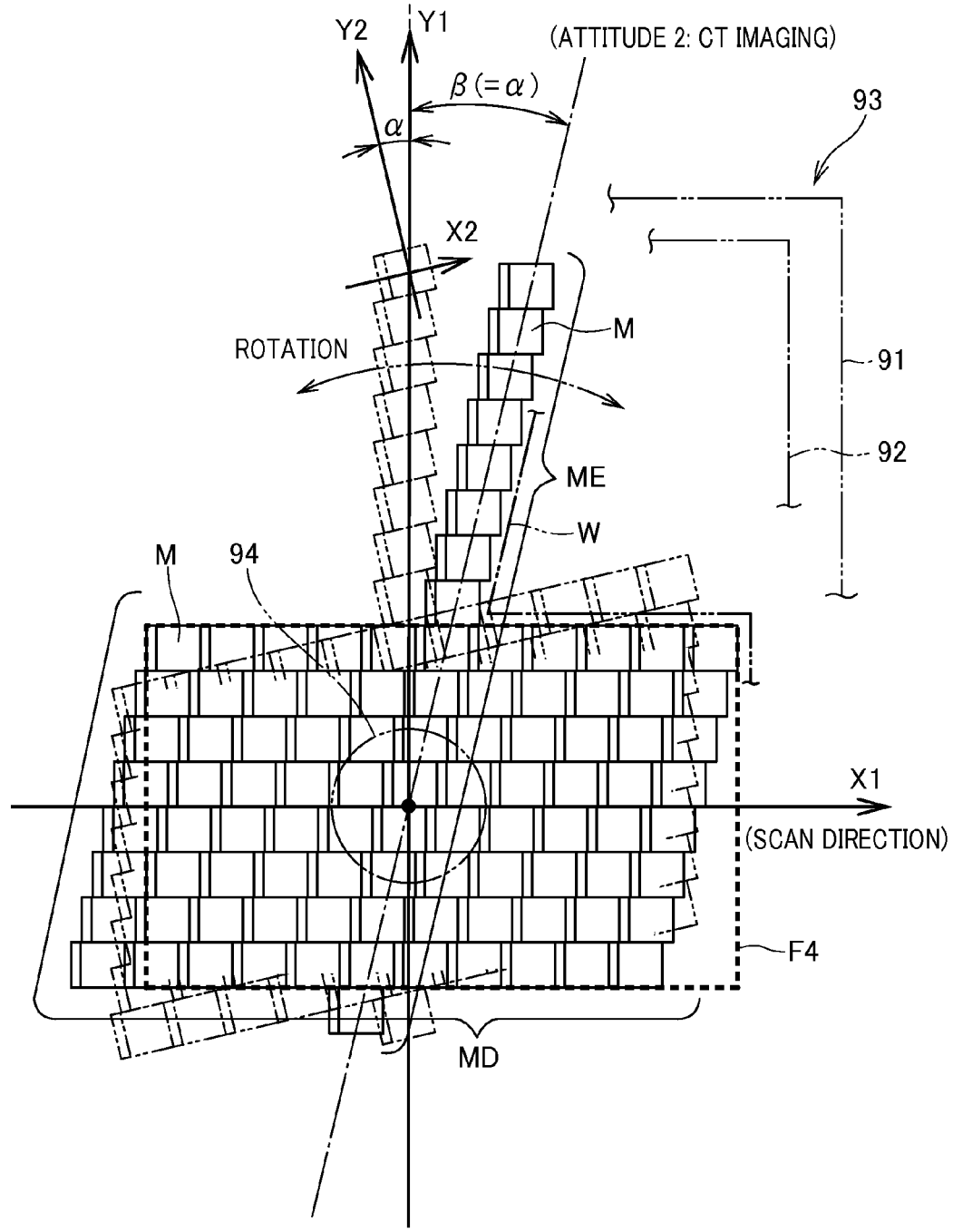
FIG. 24 is a plan view outlining a detector according to another modification.

FIG. 24 shows an X-ray detector 93 according to a second modification of the embodiments described above. As shown, the detector 93 also includes a motherboard 92 inside a housing 91. On a single plane of the motherboard 92, a module array is provided which is a combination of the array of the modules M of the detector 22 described in the first embodiment and an array of modules M in a parallelogram shape. Each of the modules M has a structure and an arrangement which are the same as those of the above embodiments.

This oblique cascaded arrangement includes a group MD of the plurality of modules M which are two-dimensionally arranged so as to form a parallelogram having two sides parallel to the first X-axis X1 (scan direction) and two sides that are oblique to the first Y-axis Y1 at an angle β (e.g., β=α and β=14.1°). The group MD of the modules M includes, as a part of it, a module array group ME which corresponds to the center module array parallel to the two oblique sides of the parallelogram and is directly and obliquely projected upward and downward. Accordingly, the X-ray incidence window W is formed in conformity with the module-arrayed structure of the "two dimension+one dimension (two dimension in terms of the pixels)".

The X-ray detector 93 is also used both in panoramic imaging and X-ray CT imaging. Therefore, the detector 93 is provided with a rotating mechanism 94. Using the rotating mechanism 94, a posture 1 is adopted in panoramic imaging. In other words, the detector 93 is rotated counterclockwise as viewed in FIG. 24 so that the angle β=0. Accordingly, the modules M as a whole are arrayed parallel to the first Y-axis Y1 in an oblique cascaded arrangement but are slanted upward to the right with respect to the first X-axis X1. In this oblique cascaded arrangement, the one-dimensionally arrayed module group ME is used for panoramic imaging.

On the other hand, using the rotating mechanism 94, a posture 2 is adopted in X-ray CT imaging. In other words, a slant by the angle β=14.1° is achieved with respect to the first Y-axis Y1. Thus, the module group MD forms a parallelogram which is parallel to the scan direction, i.e. the first X-axis X1. Signals detected by the modules of the module group MD in this state are used in X-ray CT imaging.

Thus, one detector 93 can cope with both of the modalities, enhancing general purpose properties. Although the pixels are not obliquely arrayed with respect to the scan direction in X-ray CT imaging, when a field of view F4 is attempted to be ensured, a smaller number of modules can advantageously achieve this field of view F4 than in the case of the module group MA shown in FIG. 22. The value of the angle β is also not limited to the one mentioned above.

Figure 25:
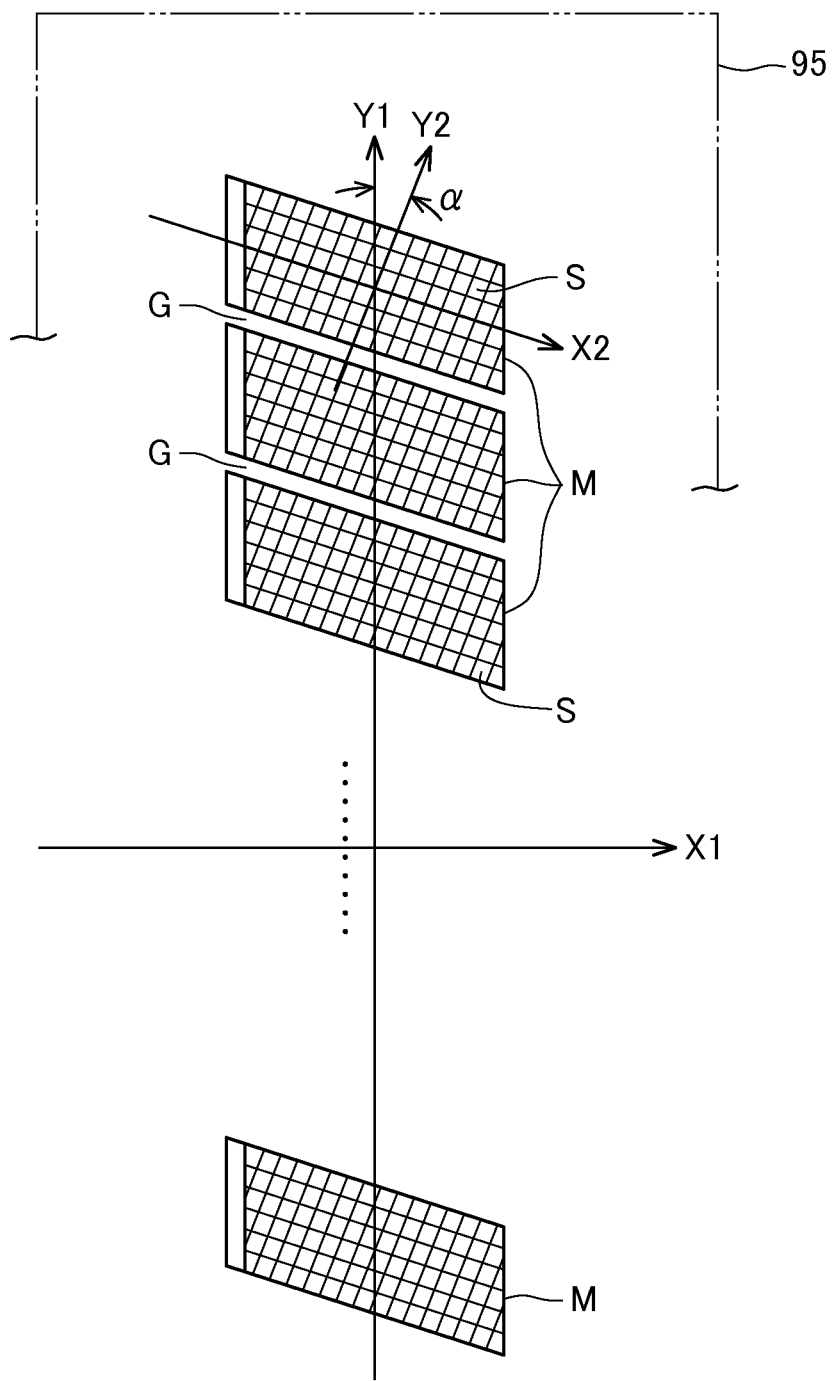
FIG. 25 is a plan view outlining a detector according to another modification.

Referring to FIG. 25, a third modification is described. This modification relates to a different arrayed structure of modules of a radiation detector to which the present invention can be applied. In an X-ray detector 95 shown in FIG. 25, a plurality of modules M are cascaded along the first Y-axis Y1, being slanted by the angle α with respect to the first X-axis X1 and the first Y-axis Y1 to provide a one-dimensional cascaded arrangement. Unlike in the embodiments and modifications described above, each module M has a detection surface in a parallelogram shape. If only the detection surface is in a parallelogram shape, the parallelogram may be the one derived from rectangle or may be the one derived from square. These modules M are arranged being cascaded with the gap G of a known width being interposed therebetween. However, in each of the modules M a plurality of detection elements S are two-dimensionally arranged along the second orthogonal-coordinate system (X2, Y2). Accordingly, scan is performed in a state where the detection elements S are each oblique to the scan direction. This will exert the advantageous effects similar to those of the square modules described so far. In each of the modules M in a parallelogram shape, pixels do not have to be necessarily formed at both end portions in the direction of the second X-axis X2, in which completely square pixels cannot be formed.

In the embodiments described above, the detection elements S and the respective data acquisition circuits 51n for all of the pixels are integrally configured by ASICs using CMOSs. However, the data acquisition circuits 51n may each be configured as circuits or devices separate from the group of detection elements S.

The present invention is not limited to the structures of the embodiments and the modifications described above but may be altered as appropriate within a scope not departing from the spirit of the present invention.

Figure 26:
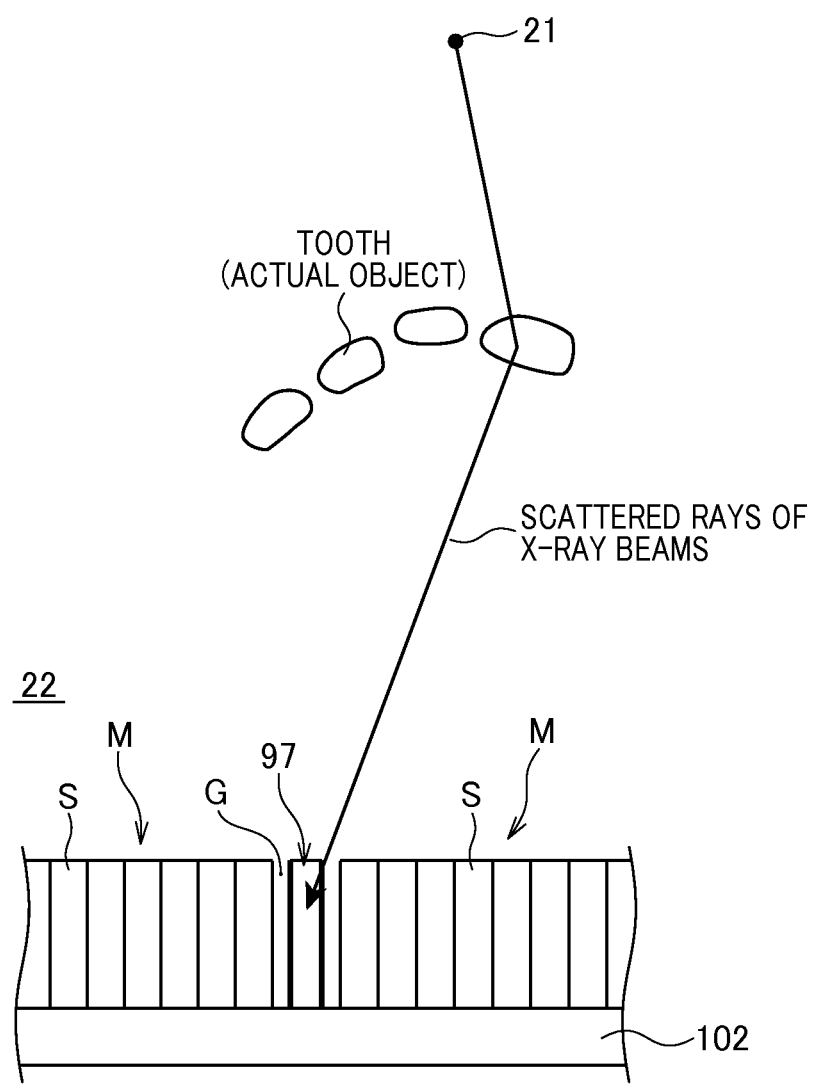
FIG. 26 is a partial view of a side of a detector, which shows a structure for suppressing influence of scattered X-rays, which is also explained as another modification.

For example, a different means may be configured as shown in FIG. 26, for decreasing the influence attributed to the presence of the gap G between the modules M of the detector 22, i.e. means for uniforming an image. As shown, a shielding member 97 having electrical insulation properties and high energy absorptive capacity may be embedded in the gap G along the side faces of the modules M. Thus, X-rays that are incident on the side faces of the modules M are decreased and uniformity of the detection sensitivity in the peripheral portions of the modules M is suppressed from being impaired as much as possible. The shielding member 97 may be formed by applying insulation coating to a material member made such as of tungsten, molybdenum or lead, which is thinner than the gap G, or by using a material member, such as a high-specific gravity ceramic plate, having high insulation properties. The provision of the shielding member 97 may be combined with the preprocessing described at step S7 of FIG. 8 to more enhance the effect of image uniformity.

Further, the gap that has to be provided between the modules may have a smaller width. To provide such a configuration, each of the pixels in the peripheral portions of each module may be enlarged by making the sensor portion (charging electrode E1, detection layer K1 and collecting electrode E2) slightly wider than the ASIC layer K2 (e.g., charge amplifier 52). Thus, the quantity of X-rays entering the gap G can be equivalently decreased to minimize the influence described above attributed to the gap G.

As described above, the pixel values obtained using the sub-pixel technique are mapped in the virtual memory space VM set in the image processor 35. The mapping may be modified as follows. This modification is based on the concern that, in arranging the plurality of modules M on the motherboard 102, variation is actually unavoidably caused and after all the width of the gap G is also varied with reference to the specified value. Specifically, after arranging the modules M, the actual value of the width of each gap G is measured using a measuring means, such as an optical measuring device. According to the measurements, the image processor 35 changes the points (i.e. pixels) of mapping the pixel values in the virtual memory space VM. Thus, the variation in the arrangement of the modules M can be absorbed by the mapping of the pixel values, and accordingly, the accuracy required for the module arrangement is released.

INDUSTRIAL APPLICABILITY

According to the present invention, it is possible to provide a radiation detector and a radiation imaging apparatus using the same, in which the detector is provided with oblique cascaded arrangement of modules, resulting in that the detection is able to reduce an X-ray exposure and detect the X-ray beams with higher resolution,

DESCRIPTION OF REFERENCE NUMBERS 1 dental panoramic imaging apparatus (radiation imaging apparatus)
3 console
21 X-ray tube (radiation source)
22 detector (radiation detector)
33 controller
35 image processor
51 data acquisition circuit
81, 90, 95 detector
97 shielding member
S detection element (pixel)
M module
VM virtual memory space

The invention claimed is:

1. A radiation detector comprising:
a plurality of modules each provided with a rectangular radiation incidence surface in which a plurality of detection elements are arrayed, each of the detection elements composing a pixel, converting an incoming radiation to an electronic data, and outputting the electronic data whose amount corresponds to an amount of the incoming radiation, wherein
the plurality of modules are mutually adjacently arranged on the same surface with a gap having a known width formed therebetween, such that the modules are arranged along at least one of a first X-axis and a first Y-axis, wherein the radiation detector is given a scan direction which is set along one of the first X-axis and the first Y-axis and the first Y-axis is perpendicular to the first X-axis; and
the plurality of detection elements of each of the modules are two-dimensionally arranged along a second X-axis and a second Y-axis which are set obliquely to the first X-axis and the first Y-axis respectively and which are perpendicular to each other,
wherein the second X-axis and the second Y-axis have a relative angle to the first X-axis and the first Y-axis respectively, the relative angle being a range of 6-20.7 degrees, the relative angle being set based on a use rate of area in the radiation incidence surface of the radiation detector, a required area rate required for uniformity correction of the data outputted from the radiation detector, and an influence rate of the known width in the scan direction, and
the radiation detector comprises a shielding member arranged in the gap between ones of the plurality of modules mutually adjacent, the shielding member having a width narrower than the gap, having a surface covered by electrical insulating material, and containing therein a material with a specific gravity of equal or higher to or than the detection elements.

2. The radiation detector of claim 1, wherein
wherein the insulating material is composed of a material produced by performing an electrical insulating process with tungsten, molybdenum, copper, lead, cadmium telluride, or material containing high specific gravity ceramic.

3. The radiation detector of claim 1, wherein the known width of the gap is an integral multiple of 1/N (N is a positive integer of 2 or more) of a size of each of the pixels.

4. The radiation detector of claim 3, wherein the plurality of modules are one-dimensionally arranged along the first X-axis or the first Y-axis.

5. The radiation detector of claim 3, wherein the plurality of modules are two-dimensionally arranged along the first X-axis and the first Y-axis.

6. The radiation detector of claim 3, wherein the plurality of modules are partially arranged one-dimensionally along the first X-axis or the second Y-axis and also partially arranged two-dimensionally along the first X-axis and the first Y-axis.

7. The radiation detector of claim 3, wherein the plurality of modules are arranged such that the modules have, as a whole thereof, an actual detection surface into which the radiation comes, the actual detection surface having an area, the modules enabling setting of an inscribed field of view to the area of the actual detection surface, an circumscribed field of view thereto, or a field of view larger than the circumscribed field of view.

8. The radiation detector of claim 3, wherein each of the plurality of modules is a module having a square detection surface in which the detection elements each being square are arranged along each of the second X-axis and the second Y-axis, the detection elements arranged along the second X- and Y-axes are the same in number.

9. The radiation detector of claim 1, wherein
each of the detection elements is configured to directly convert the radiation to the electric signal which is digital quantity, and
the detector comprises a processing circuit that processes the digital electric data to pixel data, wherein the processing circuit is configured to count the number of particles of the radiation and produce the pixel data based on a result of the counting.

10. A radiation imaging apparatus, comprising:
a radiation source;
a radiation detector provided with a rectangular radiation incidence surface in which a plurality of modules each provided with a plurality of detection elements are arrayed, each of the detection elements composing a pixel, each of the detection elements converting, pixel by pixel, an incoming radiation from the radiation source to an electronic data, and outputting the electronic data whose amount corresponds to an amount of the incoming radiation, the radiation detector regularly and repeatedly outputting, as frame data; and
image producing means for producing the frame data into image data, wherein
the plurality of modules are mutually adjacently arranged on the same surface with a gap having a known width formed therebetween, such that the modules are arranged along at least one of a first X-axis and a first Y-axis, wherein the radiation detector is given a scan direction which is set along one of the first X-axis and the first Y-axis and the first Y-axis is perpendicular to the first X-axis; and
the plurality of detection elements of each of the modules are two-dimensionally arranged along a second X-axis and a second Y-axis which are set obliquely to the first X-axis and the first Y-axis respectively and which are perpendicular to each other,
wherein the second X-axis and the second Y-axis have a relative angle to the first X-axis and the first Y-axis respectively, the relative angle being a range of 6-20.7 degrees, the relative angle being set based on a use rate of area in the radiation incidence surface of the radiation detector, a required area rate required for uniformity correction of the data outputted from the radiation detector, and an influence rate of the known width in the scan direction,
the image producing means comprises conversion means for using a virtual memory space to convert the image data to pixel values of respective pixels of the virtual memory space under a sub-pixel technique, the virtual memory space having a two-dimensional arrangement of pixels whose sizes are smaller than the pixels of the radiation detector, and
the pixels in the virtual memory space are mapped according to a coordinate system consisting of the first X-axis and the first Y-axis.

11. The radiation imaging apparatus of claim 10, wherein the virtual memory space has a two-dimensional memory space whose size corresponds to an inscribed field of view to an area of an actual detection surface, an circumscribed field of view thereto, or a field of view larger than the circumscribed field of view, the modules having, as a whole thereof, the actual detection surface into which the radiation comes, the actual detection surface having the area.

12. The radiation imaging apparatus of claim 11, wherein the virtual memory space has a two-dimensional memory space each of which pixels has a size equal to or smaller than an integral multiple of 1/N (N is a positive integer of 2 or more) of a size of each of the pixels composing each of the modules.

13. The radiation imaging apparatus of claim 12, wherein the conversion means comprises
calculation means for calculating values of the respective pixels of the virtual memory space based on area ratios of the pixel data of the frame data, the area ratios showing how largely areas of the pixel data occupy the respective pixels of the virtual memory space when the pixel data of the frame data are mapped to the virtual memory space, and
mapping means for mapping results of the calculation means to the respective pixels of the virtual memory space,
wherein the calculation means is configured to calculate the values of the pixels of the virtual memory space on the assumption that pixels positionally corresponding to the gaps between the modules in the detection surface are given a value of zero.

14. The radiation imaging apparatus of claim 12, wherein the conversion means comprises
calculation means for calculating values of the respective pixels of the virtual memory space based on area ratios of the pixel data of the plurality of frame data outputted at intervals from the radiation detector, the area ratios showing how largely areas of the pixel data occupy the respective pixels of the virtual memory space when the pixel data of the plurality of frame data are overlapped on one another in consideration of movement amounts in the virtual memory space, and
mapping means for mapping the calculated pixel values to the respective pixels of the virtual memory space,
wherein the calculation means is configure to calculate the values of the pixels of the virtual memory space on the assumption that pixels positionally corresponding to the gaps between the modules in the detection surface are given a value of zero.

15. The radiation imaging apparatus of claim 14, wherein the image producing means comprises
uniformization means for performing a process for uniformizing images reconstructed, by correcting irregularities in sensitivity in the frame data outputted from the radiation detector, the sensitive irregularities being caused due to lack of detection pixels in the gaps between the modules, and
reconstruction means for reconstructing an image using the plurality of frame data whose sensitivity irregularities have been corrected by the uniformization means.

16. The radiation imaging apparatus of claim 15, wherein the mapping means is configured to map, to the respective pixels of the virtual memory space, the results calculated by the calculation means with consideration for an actual value of the gap between the modules, the actual value being measured by measurement means.

17. A radiation detector comprising:
- a plurality of modules each provided with a rectangular radiation incidence surface in which a plurality of detection elements are arrayed, each of the detection elements composing a pixel, converting an incoming radiation to an electronic data, and outputting the electronic data whose amount corresponds to an amount of the incoming radiation, wherein
- the plurality of modules are mutually adjacently arranged on the same surface with a gap having a known width formed therebetween, such that the modules are arranged along at least one of a first X-axis and a first Y-axis, wherein the radiation detector is given a scan direction which is set along one of the first X-axis and the first Y-axis and the first Y-axis is perpendicular to the first X-axis; and
- the plurality of detection elements of each of the modules are two-dimensionally arranged along a second X-axis and a second Y-axis which are set obliquely to the first X-axis and the first Y-axis respectively and which are perpendicular to each other,
- wherein the second X-axis and the second Y-axis have a relative angle to the first X-axis and the first Y-axis respectively, the relative angle being a range of 6-20.7 degrees, the relative angle being set based on a use rate of area in the radiation incidence surface of the radiation detector, a required area rate required for uniformity correction of the data outputted from the radiation detector, and an influence rate of the known width in the scan direction, and
- the known width of the gap is an integral multiple of 1/N (N is a positive integer of 2 or more) of a size of each of the pixels.

18. The radiation detector of claim 17, wherein the plurality of modules are one-dimensionally arranged along the first X-axis or the first Y-axis.

19. The radiation detector of claim 17, wherein the plurality of modules are two-dimensionally arranged along the first X-axis and the first Y-axis.

* * * * *